(12) United States Patent
Wheeler

(10) Patent No.: US 7,071,373 B1
(45) Date of Patent: *Jul. 4, 2006

(54) TRANSGENIC UNGULATE COMPOSITIONS AND METHODS

(75) Inventor: Matthew B. Wheeler, Tolono, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/410,539

(22) Filed: Mar. 24, 1995

Related U.S. Application Data

(63) Continuation-in-part of application No. 08/063,095, filed on May 14, 1993, now Pat. No. 5,523,226.

(51) Int. Cl.
*C12N 15/00* (2006.01)
*C12N 5/00* (2006.01)
*A01K 67/00* (2006.01)
*A01K 67/033* (2006.01)
*C12P 21/00* (2006.01)

(52) U.S. Cl. .............................. 800/24; 800/8; 800/14; 800/4; 435/325

(58) Field of Classification Search .................... 800/2, 800/DIG. 1, DIG. 4, 24, 8, 14, 4; 435/172.3, 435/325, 378; 935/63, 70
See application file for complete search history.

(56) References Cited

U.S. PATENT DOCUMENTS

| | | | | |
|---|---|---|---|---|
| 5,175,383 A | 12/1992 | Leder et al. | .................... | 800/2 |
| 5,175,384 A | 12/1992 | Krimpenfort et al. | .......... | 800/2 |
| 5,175,385 A | 12/1992 | Wagner et al. | .................... | 80/2 |
| 5,523,226 A * | 6/1996 | Wheeler | .................. | 435/240.2 |
| 5,690,926 A | 11/1997 | Hogan | ....................... | 424/93.1 |

FOREIGN PATENT DOCUMENTS

| | | |
|---|---|---|
| EP | 0169672 | 1/1986 |
| GB | 2213831 | 8/1989 |
| WO | WO 90/01541 | 2/1990 |
| WO | WO90/03432 | 4/1990 ........................ 5/6 |
| WO | WO 90/03432 | 4/1990 |
| WO | WO 92/22646 | 12/1992 |
| WO | WO 94/03585 | 2/1994 |
| WO | WO94/09803 | 5/1994 |
| WO | WO95/08625 | 3/1995 |
| WO | WO95/16770 | 6/1995 |
| WO | WO95/17500 | 6/1995 |
| WO | WO95/34636 | 12/1995 ........................ 5/6 |
| WO | WO96/07732 | 3/1996 ........................ 5/6 |
| WO | WO97/20035 | 6/1997 ........................ 5/6 |
| WO | WO97/25412 | 7/1997 |
| WO | WO97/25413 | 7/1997 ........................ 5/6 |
| WO | WO97/37009 | 10/1997 |
| WO | WO98/06834 | 2/1998 |
| WO | WO98/27214 | 6/1998 .................... 15/63 |
| ZA | 9401930 | 1/1995 |

OTHER PUBLICATIONS

Kashminazaki, et al (1992) Veterinary Record 130 186-187.*
Moreadith, R.W. et al. Gene Targeting in Embryonic Stem Cells: The New Physiology and Metabolism. J. Mol. Med, 1997, 75:208-216.*
Mullins, L.J. et al. Molecular Medicine in Genetically Engineered Animals. J. Clin. Invest., 1997, 97:1557-1560.*
Pera et al. Journal of Cell Science 113: 5-10 (2000).*
Clark et al. Genome 31(2):950-955 (1989).*
Axelrod, H.R., "Embryonic Stem Cell Lines Derived from Blastocysts by a Simplified Technique," *Developmental Biology*, 101:225-228 (1984).
Bazer, F.W., et al., "Fertilization, Cleavage and Implantation," in *Reproduction in Farm Animals*, 5th ed., ed. Hafez, E.S.E., Lea & Febiger, Philadelphia, PA (1987).
Bearden, J.H., et al., "Gestation," *Applied Animal Reproduction*, pp. 85-98, Reston Publishing Company, Reston VA (1980).
Bishop, Jerry E., Sheep-Cloning Method Holds Promise of Fast Introduction of Livestock Traits, News Article, 1996.
Bleck, G.T., et al., "Single-Base Polymorphisms and DNA Sequence of the Porcine α-Lactalbumin 5' Flanking Region," *J. Dairy Sci.*, (Suppl.1):946 (1994).
Bradley, A., et al., "Formation of germline chimeras from embryo-derived teratocarcinoma cells lines," *Nature*, 309:255-256 (1984).
Brinster, et al., "Targeted correction of a mjaor histocompatibility class II Eα gene by DNA microinjected into mouse eggs," *Proc. Natl. Acad. Sci.*, 86:7087-7091 (1989).
Capecchi, Mario R., "The new mouse genetics: Altering the genome by gene targeting," *Trends in Genetics*, 5(3):70-76 (1989).
Clark, A.J., et al., "Germ line manipulation: applications in agriculture and biotechnology," *Transgenic Animals*, p. 250, Grosveld, et al., eds., Academic Press Limited (1992).

(Continued)

Primary Examiner—Anne-Marie Falk
Assistant Examiner—Thaian N. Ton
(74) Attorney, Agent, or Firm—Alice O. Martin; Barnes & Thornburg

(57) ABSTRACT

Transgenic ungulates and compositions and methods for making and using same, are provided. Central to the invention are porcine, bovine, ovine and caprine embryonic stem cell lines and methods for establishing them. Cells of such lines are transformed with exogenous genetic material of interest and then used to provide chimeric ungulates confirmed by genetic markers which have germ cells comprising the exogenous genetic material. The chimeric ungulates are bred to provide transgenic ungulates. The transgenic animals of the invention may show improved qualities and can be used to provide human proteins or peptide hormones or can be used as xenograft donors.

8 Claims, 6 Drawing Sheets

OTHER PUBLICATIONS

Clark, et al., "Expression of human anti-hemophilic factor IX in the milk of transgenic sheep," *Biotechnology*, vol. 7:487-492 (1989).

Cruz, Y.P., et al., "Origin of embryonic and extraembryonic cell linages in mammalian embryos," in *Animal Application of Research in Mammalian Development*, eds. Pedersen,, R.A., et al., Cold Spring Harbor Laboratory Press, Plainview, NY (1991).

Doetschman, T., et al., "Establishment of Hamster Blastocyst-Derived Embryonic Stem (ES) Cells," *Developmental Biology*, 127:224-227 (1988).

Ebert, K.M., et al., "Changes in Domestic Livestock through Genetic Engineering," in *Current Communications 4 Cell & Molecular Biology, Animal Applications of Research in Mammalian Development*, ed. Pederson et al., Cold Springs Harbor Laboratory Press, pp. 233-266 (1991).

Evans, M.J., et al., "Establishment in culture of pluripotential cells from mouse embryos," *Nature*, 292:154-156 (1981).

Fajfar-Whetstone, C.F., et al., "Sex Determination of Porcine Pre-Implantation Embryos via Y-Chromosome Specific DNA Sequence," *Anim. Biotech.*, 4:183-193 (1993).

Flake, A.W., et al., "Transplantation of fetal hematopoietic stem cells in utero: the creation of hematopoietic chimeras," *Science*, vol. 233 (1986).

Frohman and Martin, "Cut, paste, and save: New approaches to altering specific genes in mice," *Cell*, 56:145-147 (1989).

Gossler, A., et al., "Transgenesis by means of blastocyst-derived embryonic stem cell lines," *Proc. Natl. Acad. Sci. USA*, 83:9065-9069 (1986).

Hagen, D.R., et al., *J. Anim. Sci.*, 69:1147-1150 (1991).

Handyside, A., et al., "Towards the Isolation of Embryonal Stem Cell Lines from the Sheep," *Roux's Arch, Developmental Biology*, 196:185-190 (1987).

Hasty, et al., "The length of homology required for gene targeting in embryonic stem cells," *Molecular and Cellular Biology*, 11(11):5586-5591 (1991).

Hogan, et al., "Isolation of Pluripotential Stem Cell Lines," *Cold Spring Harbor Laboratory—Manipulating the Mouse Embryo: A Laboratory Manual*, Section E:205-218 (1986).

Hooper, M.C., *Teratocarcinomas and Embryonic Stem Cells: A Practical Approach*, ed. Robertson, E.J., IRL Press, Ltd., Oxford, UK, 51-70 (1987).

Jasin and Berg, "Homologous integration in mammalian cells without target gene selection," *Genes & Development*, 2:1353-1363 (1988).

Jeannotte, et al., "Low level of Hoxl.3 gene expression does not preclude the use of promoterless vectors to generate a targeted gene disruption," *Molecular and Cellular Biology*, 11(11):5578-5585.

Karg, H., "Manipulation of Lactation," in *Biotechnology for Livestock Production*, Plenum Press, New York and London, 19:181-206 (1989).

Karg, H., "Manipulation of Growth," in *Biotechnology for Livestock Production*, Plenum Press, New York and London, 18:159-180 (1989).

Kollias, G., et al., "The study of gene regulation in transgenic mice," *Transgenic Animals*, p. 92, Grosveld, et al., eds., Academic Press Limited (1992).

Lewin, H.A., et al., "Mapping Genes for Resistance to Infectious Diseases in Animals," in *Gene-Mapping Techniques and Applications*, Marcel Dekker, Inc., 13:283-304 (1991).

Mansour, et al., "Disruption of the proto-oncogene int-2 in mouse embryo-derived stem cells: A general strategy for targeting mutations to non-selectable genes," *Nature*, 336:348-352.

Martin, G.R., "Teratocarcinomas and Mammalian Embryogenesis," *Science*, 209:768-776 (1980).

Martin, G.R., "Isolation of a Pluripotent Cell Line from Early Mouse Embryos Cultured in Medium Conditioned by Teratocarcinoma Stem Cells," *Proc. Natl. Acad. Sci. USA*, 78(12):7634-7638 (1981).

Martin, P., et al., "Improvement of milk protein quality by gene technology," *Livestock Production Science*, 35:95-115 (1993).

McLaren, A., et al., *Nature*, 224, pp. 238-240 (1969).

Mintz, B., *Science*, 148, 1232-3 (1965).

Morgenstern and Land, *Nucleic Acids Res.*, 18:3587-3596 (1990).

Mortensen, et al., "Production of homozygous mutant ES cells with a single targeting construct," *Molecular and Cellular Biology*, 12(5):2391-2395 (1992).

Nichols, J., et al., "Establishment of germ-line-competent embryonic stem (ES) cells using differentiation inhibiting activity," *Development*, 110:1341-1348 (1990).

Notarianni, E., et al., "Maintenance and differentiation in culture of pluripotential embryonic cell lines from pig blastocysts," *J. Reprod. Fert., Suppl.* 41:51-56 (1990).

Papaioannou, V.E., et al., "Growth and differentiation of an embryonal carcinoma cell line (C145b)," *Embryol. exp. Morph.*, 54, pp. 277-295 (1979).

Phillips, R.W., et al, Models, pp. 437-440 in *Swine in Biomedical Research*, ed. Tumbleson, M.E., vol. 1 (Plenum Press, New York), (1986).

Piedrahita, J.A., et al., "Influence of Feeder Layer Type on the Efficiency of Isolation of Porcine Embryo-Derived Cell Lines", *Theriogenology*, 34(5):865-877 (1990).

Piedrahita, J.A., et al., "On the Isolation of Embryonic Stem Cells: Comparative Behavior of Murine, Porcine and Ovine Embryos," *Theriogenology*, 34(5):879-901 (1990).

Polge, C., "Embryo transplantation and preservation," pp. 277-291 in *Control of Pig Reproduction*, Cole, D.J.A., et al., eds., Butterworth Scientific, London (1982).

Robertson, E., et al., "Germ-line transmission of genes introduced into cultured pluripotential cells by retroviral vector," *Nature*, 323:445-448 (1986).

Robertson, E.J., "Pluripotential stem cell lines as a route into the mouse germ line," *Trends Genet.*, 2:9-13 (1987).

Robertson, E.J., "Embryo-derived Stem Cell Lines," *Teratocarcinomas and Embryonic Stem Cells: A Practical Approach*, Chap. 4(4.4.2):92, ed. Robertson, E.J., IRL Press (1987).

Rohrer, G.A., Alexander, L.J., Keele, J.W., Smith, T.P., Beattie, C.W., "A Microsatellite Linkage Map of the Porcine Genome," *Genetics*, 136:231-245 (1994).

Rossant, J., et al., "The developmental potential of a euploid male teratocarcinoma cell line after blastocyst injection," *J. Embryol. exp. Morph.*, 70, 99-112 (1982).

Rossant, J., et al., "The relationship between embryonic, embryonal carcinoma and embryo-derived stem cells," *Cell Differentiation*, 15:155-161 (1984).

Rudnicki, M.A., et al., "Teratocarcinomas and Embryonic Stem Cells: A Practical Approach," *Methods and Induction of Differentiation in Embryonal carcinoma Cell Lines*, pp. 19-49, ed. Robertson, IRL Press Ltd., Oxford, England (1987).

Schook, L.B., et al., "Mapping Genes for Growth and Development," 4:75-92, in *Growth of the Pig,* ed. Hollis, CAB International, Wallingford, UK (1993).

Sims, M.M., et al., "Production of Fetuses from Totipotent Cultured Bovine Inner Cell Mass Cells," *Theriogeneology,* 39:313 (1993).

Smith, A.G., et al., "Buffalo Rat Liver Cells Produce a Diffusible Activity which Inhibits the Differentiation of Murine Embryonal Carcinomas and Embryonic Stem Cells," *Dev. Biol.,* 121:9 (1987).

Stevens, L.C., "The development of transplantable teratocarcinomas from intratesticular grafts of pre- and post-implantation mouse embryos," *Dev. Biol.,* 21, 364-382 (1970).

Strojek, R.M., et al., "A Method for Cultivating Morphologically Undifferentiated Embryonic Stem Cells from Porcine Blastocysts," *Theriogenology,* 33(4):901-913 (1990).

Talbot, N.C., et al., "Alkaline phosphatase staining of pig and sheep epiblast cells in culture," *Molecular Reproduction and Development,* 36:139-147 (1993).

Thomas, et al., "High-fidelity gene targeting in embryonic stem cells by using sequence replacement vectors," *Molecular and Cellular Biology,* 12(7):2919-2923 (1992).

Thomas, K.R., et al., "Site-Directed Mutagenesis by Gene Targeting in Mouse Embryo-Derived Stem Cells," *Cell,* 51:503-512 (1987).

Wall, R.J., et al., "High-level synthesis of a heterologous milk protein in the mammary glands of transgenic swine," *Proc. Natl. Acad. Sci. USA,* 88, 1696-1700 (1991).

Ware, C.B., et al., "Development of embryonic stem cell lines from farm animals," *Biology of Reproduction,* supplement, vol. 38 (1988).

Webel, S.K., et al., "Synchronous and asynchronous transfer of embryos in the pig," *J. Animal Science,* 30:565-568 (1970).

Wobus, A.M., et al., "Characterization of a Pluripotent Stem Cell Line Derived from a Mouse Embryo," *Exp. Cell Res.,* 152:212-219 (1984).

Wurst, W., et al., "Production of targeted embryonic stem cell clones," *Gene Targeting A Practical Approach,* p. 33, Joyner, A.L., ed., IRL Press (1993).

Yates, et al., *Nature,* 313:811-815 (1985).

\* cited by examiner

TRANSGENIC UNGULATE COMPOSITIONS AND METHODS

This application is a continuation-in-part of U.S. Ser. No. 08/063,095 filed May 14, 1993, herein incorporated by reference and issued Jun. 4, 1996 as U.S. Pat. No. 5,523,226.

BACKGROUND OF THE INVENTION

This invention relates compositions and methods for making ungulate embryonic stem cells, producing chimeric ungulates from the stem cells, and deriving transgenic ungulates from the chimeras.

Although transgenic animals have been produced by several different methods in several different species, methods to readily and reproducibly produce transgenic large mammals such as ungulates at reasonable costs are still lacking.

Current methods for producing transgenic large animals such as ungulates, notably of the Order Artiodocylia, that includes, pigs, cattle, sheep and goats, have limitations that prevent them from becoming widespread in the commercial arena. Such methods include microinjection of ova and embryonic transduction with a recombinant molecule, for example, via a retroviral vector which includes a transgene.

To illustrate the high costs of such methods, microinjecting swine ova with genetic material to produce transgenic swine, costs between $25,000 to $250,000 to produce a single transgenic animal line. Another problem of microinjection is that it is a technically difficult procedure with an unacceptably low success rate. Furthermore, DNA transferred by microinjection is incorporated at random in the genome, usually in tandem linear arrays of multiple copies of the transgene. These limitations have resulted in animals being produced in which 1) the transgene is not incorporated at all, 2) the transgene is incorporated but not expressed, 3) the transgene is incorporated but expressed transiently or aberrantly. Rarely is the transgene incorporated and expressed normally. Also, the incorporation of transgenes in a host genome may result in the disruption of an endogenous gene by a so-called insertional mutation, which disrupts some aspect of the host's development, growth or normal physiology. Furthermore, random insertion results in difficulties controlling how the transgene will be regulated because flanking sequences upstream and downstream of the inserted transgenic DNA construct which can alter the control of the transgene expression are randomly associated with the transgene.

A method to generate transgenic animals, the use of transformed embryonic stem cells (ES-cells), has shown certain advantages over other methods when used to produce mouse chimeras, from which transgenic mice are derived. After they are isolated, ES-cells may be grown in vitro for many generations, producing unlimited numbers of identical ES-cells. These cells, when combined by fusion or injection with an early embryo, are capable of becoming part of the embryo and participating in the normal developmental process. The resultant animal is a chimera composed of two genotypes (Bradley et al., 1984).

An advantage of ES-cells is that they can be genetically manipulated in vitro. ES-cells may be transformed by introducing exogenous DNA into the ES host cells via electroporation or a biolistic approach. Following transformation, individual ES-cell clones may be screened in vitro for the incorporation and proper expression of the exogenous DNA before being used to produce chimeric embryos (Thomas et al., 1987).

The genetic manipulation of ES-cells in culture and the subsequent generation of transgenic animals via intermediate chimeric animals derived from the genetically manipulated ES-cells provide a particularly important advantage of ES-cell technology. Gene knockouts and gene replacements are methods of genetic manipulation via homologous recombination that have been carried out in microorganisms, but have only been practiced in mammalian cells within the past decade. These techniques allow for the targeted inactivation (knockout) of a particular gene, as well as for the replacement of a particular gene with an altered version of the gene, or with another gene. Such knockouts and replacements allow for alterations in the properties of cells and animals that cannot be readily achieved in any other way. The practice of mammalian gene knockouts and gene replacements, including the design of nucleic acid molecules and the detection of successfully altered mammalian cells is discussed in numerous publications, including Thomas et al., 1987; Jasin and Berg, 1988; Mansour et al., 1988; Brinster et al., 1989; Capecchi, 1989; Frohman and Martin, 1989; Hasty et al., 1991; Jeannotte et al., 1991; Mortensen et al., 1992; and Thomas et al., 1992. Therefore, both genetically novel and useful chimeric and transgenic animals may be produced.

Gene knockouts and gene replacements can be achieved through microinjection of mammalian zygotes. However, the number of zygotes that must be injected to practice these methods in this way are so high and the injections are so technically demanding as to render this approach extremely difficult and only one report of its successful accomplishment has ever been published (Brinster et al., 1989). Large enough numbers of ES-cells can be grown in culture and conveniently genetically manipulated by recombinant techniques in vitro to allow the routine production of gene knockout and/or gene replacements in the ES-cells and thereby in animals derived from the ES-cells.

ES-cell clones containing the transferred DNA can be selected and used for blastocyst injection. The ability to screen and select transformed ES-cells in vitro is one of the most important reasons for utilizing this strategy to produce transgenic animals. Use of whole animals proceeds only after it is known that the desired transformation was successful. This procedure minimizes in vivo failures, which are more expensive than in vitro tests and take longer to produce results.

A chimeric organism is one that is a mixture of cells which differ in their genetic complements. When transformed ES-cells are used to make chimeric embryos, some of these cells may be incorporated into the gonads of the chimera and participate in the formation of sperm and ova. Incorporation of the transgene into a gamete permits germ line transmission. Consequently, some of the descendants produced by chimeric individuals will be transgenic (Gossler et al., 1986; Robertson, 1987). A transgenic animal has the transgene in all of its cells, although the transgene is not necessarily expressed. It is not usually the individual that develops from the chimeric embryo that is transgenic, but rather offspring of that individual. This is an important distinction in as much as the chimeric individual can act as founder stock to produce many transgenic individuals that carry the desirable gene(s), but the chimera is not transgenic. However, the chimera is useful for the recovery of, new or heterologous genetic expression products, organs and the like.

ES-cells have been used to produce transgenic lines of mice that through homologous recombination have genes inserted into their genome at pre-selected sites. The strategy of creating animals with specific genomic changes has immense potential for genetic engineering in developing commercially valuable plants and animals, and in furthering understanding of the genetic control of mammalian development. However, the ES-cell method has not been successfully applied to production of larger transgenic mammals, for example, transgenic ungulates. A likely reason for the failure to extrapolate methods from mice to larger animals is the difference in developmental stages of the species. For example, the embryonic disc is not a solid mass in swine as it is in a 5-day old mouse.

Piedrahita et al. (1990a and b) isolated potential swine stem cells, but were unable to maintain lines or to demonstrate these cells' pluripotentiality. Pluripotent cells are defined as cells that are capable of being induced to develop into several different cell types. True totipotent embryonic cells are those capable of being induced to develop into any cell type present in an entire animal, that is, they have the potential to directly produce an entire animal. Ovine embryos did not produce ES-like cells at all. Porcine cell culture doubling time was 80 hours which is long relative to that of mouse ES-cells. The authors believed their presumptive porcine ES-cells were different from mouse ES-cells in morphology and behavior.

Notarianni et al. (1990) reported methods to produce transgenic pigs by use of pluripotent stem cells, but did not convincingly show that pluripotent embryonic stem cells were produced. Chimeric pigs were not reported as an intermediate step toward the production of a transgenic pig.

In International Publication No. WO90/03432, (hereinafter the "Evans" patent) and other publications from the Evans group, the conclusion was that "methods . . . for the isolation of embryonic stem cells from mouse embryos and successfully applied to hamster embryos are NOT applicable to ungulate embryos . . . " (page 6) referring in particular to identification and isolation of stem cells, and predicted that ungulate "stem cells . . . would not necessarily resemble mouse embryonic stem cells in morphology or growth characteristics." (page 7) The morphological description and figures illustrating some of the pig "selected cells" group, are more reminiscent of epithelial cells, than of embryonic stem cells from other organisms such as the mouse. Indeed, the authors state the "ES" cells from pigs are morphologically dissimilar from mouse ES-cells. Also, no biochemical tests were done to confirm that the selected cells were not differentiated. Chimeric animals were not shown as evidence that cells could differentiate into several cell types (pluripotency).

Even if some embryonic stem cells were actually mixed into the "selected" cell population reported by Evans, use of these cell populations to produce chimeric pigs would be expected to be relatively inefficient because chance would dictate whether an embryonic stem cell would be included in the material transferred to a host embryo. The probability of inclusion would be expected to be proportional to the percentage of embryonic stem cells in the mixed culture. The lack of a culture substantially enriched for ES-cells would lead to inefficient and unpredictable results. Moreover, the method disclosed could not be described as "a method to produce embryonic stem cells," which implies substantial homogeneity and reproducibility, neither of which were demonstrated.

Evans teaches that a feeder cell layer is necessary for cell growth, and teaches away from the use of conditioned medium or growth factors. A feeder layer and the use of conditioned media were part of the methods of Piedrahita et al. (1990a and b) and Gossler (1986).

Strojek (1990) describes methods and results similar to those of Evans. Trophoblastic cells and non-homogeneous cultures derived from swine embryos were disclosed.

Handyside (1987) attempted to produce chimeric sheep from embryonic stem cells, but was admittedly unsuccessful. Flake (1986) produced chimeras from sheep, but resorted to in utero transplants rather than ES transfer.

Doetschman et al. (1988) identified "embryonic stem cells" from hamsters by growing them on mouse embryonic fibroblast feeder layers. Pluripotency was determined by differentiation in suspension cultures.

Ware (1988) reported embryo derived cells from "farm animals" growing on Buffalo Rat Liver (BRL) and mouse primary fetal fibroblasts.

Wall et al. (1991) suggested using transgenic swine as factories to produce biological products, but did not teach how to accomplish this goal.

Attempts to use embryonic carcinoma cells to produce chimeric mice by introducing such cells into an embryo, have had only limited success. Embryonal carcinoma cells were originally derived from embryonic cell tumors or teratocarcinomas (Stevens, 1970). Rossant and Papaioannou (1984) showed that both ES and ES-cells may differentiate in vitro into similar types. However, the formation of chimeric embryos exhibiting phenotypically normal development using ES-cells is usually low (Papaioannou et al., 1979; Rossant and McBurney, 1982), whereas ES cells are more efficient at producing chimeric mice (Bradley et al., 1984). In a variation on these methods, Martin (1981) reported growing mouse stem cells in media conditioned by the growth of teratocarcinoma cells. However, employing cancer cells in a growth environment is not likely to be palatable to the general public if such transgenic animals are ultimately to be used for products for human use, for example, food, or organs for transplants.

Improved methods for the production of chimeric and transgenic ungulates are clearly needed. A simple and efficient method is desirable to reduce costs and improve throughput. Chimeric and transgenic animals are useful as models for diseases for the testing of pharmacological agents prior to clinical trials or the testing of therapeutic modalities. Another advantage is that more desirable qualities in farm animals may be produced by introducing transgenes with suitable expression products to improve qualities. These desirable qualities include increased efficiency in feed utilization, improved meat quality, increased pest and disease resistance, and increased fertility.

Chimeric and transgenic animals are an alternative "factory" for making useful proteins by recombinant genetic techniques. Large animals such as pigs, cattle, sheep, and goats are potential factories for some products not obtainable from recombinant hosts such as microorganisms or small animals. Examples of such products are organs which are transplantable into humans.

Embryonic stem cell transfer to produce transgenic animals would be an improvement over available methods. A reason that embryonic stem cell-mediated gene transfer has not been employed in domestic livestock is the lack of established, stable embryonic stem cell lines available from these species. The availability of ES-cell lines would provide feasible methods to produce transgenic animals. However, development of ES-cell lines from livestock species is an extremely difficult process.

The early developmental embryonic morphologies of rodents (including mice) and ungulates (including swine) are quite distinct, particularly at the blastocyst stage. For example, the rodent blastocyst forms an egg cylinder, a tubular structure, while the ungulate blastocyst forms a developmentally equivalent flattened embryonic disk. The differences in the shapes of these otherwise equivalent structures contributes to the very different properties exhibited by the cells of rodent and ungulate blastocysts. These differences are most evident in vivo during the massive reorganization of cellular distribution that characterizes gastrulation in all animals. The migration and shape changes that the embryonic cells of rodents and ungulates must undergo during early development, and particularly during blastulation and gastrulation, are thus very different.

Differences in the properties of rodent and ungulate embryonic cells are also believed to be associated with the differences in placentation in these two groups of animals. Rodent trophoblast cells (the cells of the blastocyst that later form the placenta) are invasive in vivo and in vitro, while ungulate trophoblast cells are not invasive, and thus behave differently from rodent trophoblasts when cultured in vitro. With regard to the present invention, it is especially significant that in parallel with their different properties in vivo, many of the equivalent cells of rodent and ungulate embryos display different properties in vitro, as described above for trophoblast cells.

Thus, while the early embryonic development of all ungulates is morphologically identical, the differences between ungulate and rodent embryonic cells in vivo and in vitro have led to uncertainty in the art regarding the appropriate morphologic criteria to be applied to guide 1) the choice of ungulate embryonic cells to be isolated from embryos; 2) the selection of cells to be picked for expansion into useful ungulate ES-cell cultures; and 3) the selection of useful ungulate ES-cell cultures for continued propagation. These differences between ungulate and rodent embryonic cells in vivo and in vitro account for the significant differences in the practice (in accordance with the present invention) of embryonic stem cell isolation in ungulates, compared to the practice (as known in the art) of embryonic stem cell isolation in rodents.

Another problem in extrapolating from mice to ungulates, such as swine, is that exactly analogous developmental stages do not exist in the embryos of mice compared to ungulates. In ungulates, growth is generally slower, and the early embryonic ectoderm is present in a discoid arrangement, not as a solid mass as in the 5-day old mouse embryo.

In the present invention, limitations of the art are overcome by the production of stable, pluripotent ungulate embryonic stem cell cultures. These cell cultures are used to make chimeric ungulates, an intermediate step in producing a transgenic ungulate. Aspects of the invention differ from the art in, for example, culture conditions, validation of potency, and production of a chimera.

Several methods have been reported for the validation of ES cell lines from mammals. Studies in mice and Syrian Golden Hamsters have used cell morphology, biochemical markers, the ability to differentiate into various cell and tissue types and participation in embryonic development as criteria for validating the stem cell nature of embryonic cell lines. In swine, there have been several reports of the isolation of embryonic cell lines and inner cell mass cells from blastocysts. The criteria used for validation of an undifferentiated ES cell phenotype in these studies have included morphology, ability of the cells to differentiate in vitro into various cell and tissue types, and limited embryonic cell analysis of biochemical markers via immunocytochemistry and enzyme assays. However, none of the reported cell lines have produced chimeric offspring after the reintroduction of these cells into pre-implantation porcine embryos. A preferable validation for ES cells is their participation in embryonic development resulting in live chimeric offspring. The present invention is the first confirmed production of chimeric swine from ES cells.

SUMMARY OF THE INVENTION

The present invention overcomes problems and limitations in the art of producing chimeric and transgenic ungulates by presenting a novel and reproducible method which includes use of stable, embryonic stem (ES) cell lines as host vehicles for gene transfer into host embryos to form chimeras. A novel aspect of the invention is validation of ungulate chimeras produced by means of embryonic stem cell transfer into a recipient embryo, as well as the first production of genetically confirmed chimeric ungulates. The invention relates the chimeric embryos that are developed and bred to produce transgenic ungulates. Ungulates include swine, cattle, sheep and goats. Ungulates offer some distinct advantages over other species for the production of chimerics and transgenics useful for clinical purposes because they are immunologically and physiologically more similar to humans (swine, for example, Phillips and Tumbleson, 1986).

A method for making a chimeric ungulate to be used in the invention includes introducing an ungulate embryonic stem (ES) cell that has a first genetic complement into a host embryo of the same species as the embryonic stem cell. A suitable embryonic stem cell is pluripotent, but a preferred cell is totipotent. Totipotent stem cells are preferred because these cells can be induced to develop into an entire embryo. Pluripotent stem cells are those shown to produce a host structure from any one of the three germ cell layers: endoderm, ectoderm, mesoderm. Totipotent stem cells are also pluripotent, but the converse is not necessarily true. The embryonic stem cell is generally introduced into the embryo at a pre-implantation stage, preferably at the blastocyst or morula stages.

The host embryo has a second genetic complement, which is generally different from the first genetic complement. A genetic complement may designate herein all genes present, or may designate a particular gene or genes of interest. Therefore, a complement may be "different" because it has a different allele of a gene, or a different gene or genes and may be from a different species. To obtain an adult chimeric animal, in particular one capable of reproducing a transgenic line, the host embryo with the ES-cell is placed in an environment suitable for the completion of development to a stage appropriate for a particular application. To confirm chimerism, selectable markers may be introduced with the first genetic complement. Use may also be made of inherent markers such as microsatellite polymorphisms and Y-chromosome specific nucleotide sequences. To produce transgenic animals, the chimera must be reproductively functional. However, there are uses for the chimeric ungulates even if they do not produce transgenic animals.

An embryonic stem cell may be derived from a first breed of ungulates and the host embryo may be derived from a second breed of the same species as the first breed. By "derived" is meant the cell was produced by a method in which the embryo source was from a particular breed. In an illustrative embodiment, the first breed and the second breed are swine. In particular, the first breed of swine is the Meishan breed, and the second breed of swine is the Duroc breed.

The first genetic complement is generally different from the second genetic complement. The first genetic complement is preferably an exogenous nucleotide segment stably integrated into the original genetic complement of the embryonic stem cell, for example, by site-specific recombination.

An example of a first genetic complement of this type is a nucleotide segment capable of being expressed to provide a protein in recoverable form from the chimeric ungulate produced by methods of the present invention. The nucleotide segment encodes a protein which includes human Factor IX, human blood proteins, human hormones, human growth factors, human cytokines, human enzymes, human hormone receptors, human binding proteins, antigens, translation factors, transcription factors, onco-proteins, or protooncoproteins, human milk proteins, and human muscle proteins.

The first genetic complement may include a nucleotide segment that, when expressed, improves qualities of an ungulate, e.g., carcass weight and composition, milk production, disease resistance, and the like.

The embryonic ungulate stem cell may include an exogenous nucleotide segment which encodes a selectable marker. Examples of a suitable marker are hygromycin (Hph) (Yates et al., 1985), puromycin (Pac) (Morgenstern and Land, 1990) and neomycin (neo). Other selectable markers include ada (adenosine deaminase) and dHFR (dihydrofolate reductase). A marker is a well-established means to trace the descent of linked transgenes of interest.

Embryonic stem cells are obtained from a culture of embryonic stem cells. The present invention relates to a method of purifying an embryonic stem cell culture and isolating an embryonic stem cell from the culture. The method includes culturing dissociated cells from an ungulate embryo in conditioned stem cell medium in the absence of a feeder layer to form a first culture. Cultures may also be initiated using a feeder layer. The dissociated cells are obtained from an ungulate embryo which was developed in vitro in stem cell medium (SCM) or CSCM medium with or without a feeder layer. Medium conditioned by Buffalo Rat Liver cells is designated BRL/CM and is suitable for this purpose. Vitamins, amino acids and antibiotics are present in stem cell conditioned medium (CSCM). A suitable stem cell conditioned medium (CSCM) contains approximately 40% of stem cell medium (SCM) and approximately 60% of Buffalo Rat Liver Cell conditioned medium (BRL/CM). In summary, embryos will grow on:

1. SCM and a feeder layer;
2. CSCM;
3. CSCM and a feeder layer; or in
4. Whitten's medium.

Modified BECM is used to flush and hold embryos for micromanipulation.

Embryonic stem cells will grow on:

1. CSCM; a feeder layer is optional;
2. SCM and a feeder layer.

The embryo culture is subcultured until a second stable culture with morphological features and growth parameters characteristic of an embryonic stem cell culture is established. A stable cell culture is one which maintains its morphological characteristics and modal chromosome number, over repeated subcultures. Morphological characteristics include both individual cell and culture appearance (growth patterns on a solid surface). To be useful, cultures also should survive repeated subcultures. Subculturing up to passage number 44 has been achieved using the methods of the present invention.

An embryonic stem cell is by definition negative when assayed for the presence of a structural protein such as cytokeratin 18 or vimentin which are only present in a differentiated cell. An embryonic stem cell is negative when assayed for the presence of an antigen such as a neurofilament, a glial fibrillar acidic protein, keratin or desmin, which are only present in a differentiated cell. A suitable neurofilament to assay includes a protein with a molecular weight of 68, 160 or 200 kd.

The morphological features of the ES-cells isolated from a stable culture comprise a round shape, as observed with the light microscope, a diameter of approximately 8–15 microns, and a cytoplasmic to nuclear diameter ratio of approximately 10–25:75–90. Colony diameters generally are in the range of 0.08 to 1.5 mm. The growth parameters of the culture itself include a doubling time of approximately 18–36 hours and growth in a multilayer rather than a monolayer. The invention relates an embryonic ungulate stem cell as defined herein isolated from the cultures described herein.

A culture is designated as an embryonic stem cell culture if at least 50% of the cells visible on the surface of the culture, preferably 70–80%, exhibit the morphology disclosed herein as characteristic of "ES-cells." Cells are selected ("plucked") from areas in the culture that exhibit ES-cell morphology, for further subculturing to isolate and purify ES-cell cultures. Because these undifferentiated cells may differentiate, morphological heterogeneity may be observed. Cultures that have a relatively high percentage of differentiated cells are not suitable.

Using the methods of the present invention, an embryonic stem cell culture is produced which consists essentially of a type of cell that is capable of forming a teratoma or a teratocarcinoma when introduced into a host immunodeficient mammal such as a mouse. For this assay, a presumptive embryonic stem cell from a culture is introduced into an immunodeficient mammal. If an appropriate tumor is formed in the immunodeficient mammal from the embryonic stem cell, it is inferred that the culture includes embryonic stem cells. The immunodeficient mammal is generally a SCID mouse, a nude mouse or nude rat. An appropriate tumor is one that, for example, is shown to relate genetically to the ES-cell.

A method for determining the cell types in which a genetic complement is expressed, using ES-cells includes the following steps:

(a) introducing an ungulate embryonic stem cell which comprises the genetic complement, usually a transgene, into an immunocompromised mammal to produce a tumor;

(b) placing the tumor in suitable conditions to allow the tumor to differentiate into a plurality of recognizable cell types and to express the genetic complement; and (c) analyzing the differentiated cell types to determine in which cell types the genetic complement is expressed. An aspect of the invention is a tumor cell which expresses a transgene and was derived from an ungulate embryonic stem cell that had been introduced into an immunodeficient mammal.

In an illustrative embodiment, the source of an isolated ES-cell and ES-cell line is an embryo of a swine line selected from the group consisting of Meishan, Duroc and Yorkshire.

In an illustrative embodiment, stable cell lines were derived from cultures of swine embryonic stem cells. Exemplary cell lines designated D195, 1192M, and M175F are described herein.

The invention relates a chimeric ungulate produced according to the methods of the present invention. The methods include transferring a nucleus from an embryonic stem cell into an ungulate host cell from which a transgenic or chimeric embryo develops. A suitable host cell includes an enucleated ungulate ovum and an enucleated ungulate embryonic cell.

A method of making a transgenic ungulate is an aspect of the present invention. A transgenic ungulate descended from a chimeric ungulate is produced by breeding the chimeric ungulate. A transgenic animal results if there was germ cell chimerism in the parent chimera, and a gamete in the chimera including the genetic complement of the embryonic stem cell used to form the chimera, is used to produce an offspring.

A method of making an ungulate from which tissues can be used as a xenograft includes the following steps:
 (a) incorporating the genetic complement from an embryonic ungulate stem cell into a recipient ungulate embryonic cell, to form a chimeric ungulate, wherein said genetic complement renders tissue from a chimeric ungulate histocompatible with a recipient for the xenograft (see, for example, PCT patent publication Nos. 93/02188 and 94/00560); and
 (b) breeding the chimeric ungulate to form a transgenic offspring which includes the tissues for the xenograft. Both the chimeric and the transgenic ungulates are useful for xenograft as can be seen in the photograph of chimeric ungulate herein, large sections of the chimeric may express a single genotype, and that genotype may confer a desirable characteristic on the large sections. The large sections or products produced by the sections may be extracted from the ungulate for use, for example, as xenografts.

The present invention relates a method of using a chimeric or transgenic ungulate to produce an exogenous protein, said transgenic ungulate having a genetic complement which comprises a nucleotide segment capable of providing said exogenous protein, said method comprising exposing said ungulate to conditions wherein the nucleotide segment is activated to provide said exogenous protein in a recoverable form in body fluid or tissue, and recovering said protein from said body fluid. A suitable body fluid is milk secreted from a female ungulate. One particularly important application of this technology is the use of ungulates as biological reactors or factories to produce human proteins necessary for treatment of genetic of other diseases. Transgenic swine have been shown to produce more than 1 g/L of a foreign heterologous milk protein (Wall et al. 1991). Since swine may potentially produce up to 10 kg of milk per day and lactation lasts 7 weeks, one sow may produce 1 kg of a human protein such as clotting factor IX during her lactation (Wall et al., 1991).

An ungulate embryo including an ES-cell is within the scope of the present invention, as is a clone of embryos derived from the embryo. Included is a chimeric embryo which includes a cell derived from an embryonic stem cell, and an embryo made by transferring a nucleus of an isolated embryonic stem cell into a recipient cell from the same species as the embryonic stem cell. Suitable recipient cells include an enucleated swine embryonic cell and an enucleated swine ovum. The embryo preferably has an exogenous nucleotide segment stably integrated into its genetic complement. The nucleus of an ungulate embryonic stem cell and progeny of the chimeric animal are also aspects of the invention.

BRIEF DESCRIPTION OF DRAWINGS

FIG. 3 includes FIGS. 3A, 3B and 3C which are photographs of chimeric pigs.

DETAILED DESCRIPTION OF THE PREFERRED EMBODIMENTS

Figure 1A:
FIG. 1(A) shows a photograph of a nest of undifferentiated cells in an established cell line at 250× magnification (FIG. 5A, Evans patent, this photograph is the same as FIG. 3A from Notarianni et al., 1990, the source of this photograph, i.e., FIG. 5A of the Evans patent=FIG. 3A of Notarianni et al., 1990)
Figure 1B:
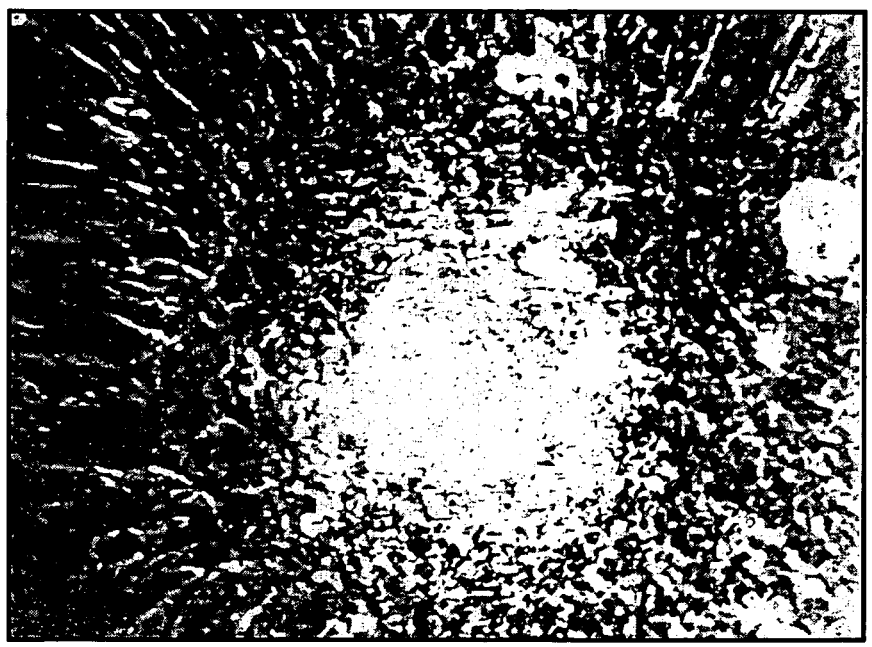
FIG. 1(B) is a photograph of a cluster or nest of undifferentiated "embryonic stem cells" from an established cell line of the present invention at 200× magnification.
Figure 1C:
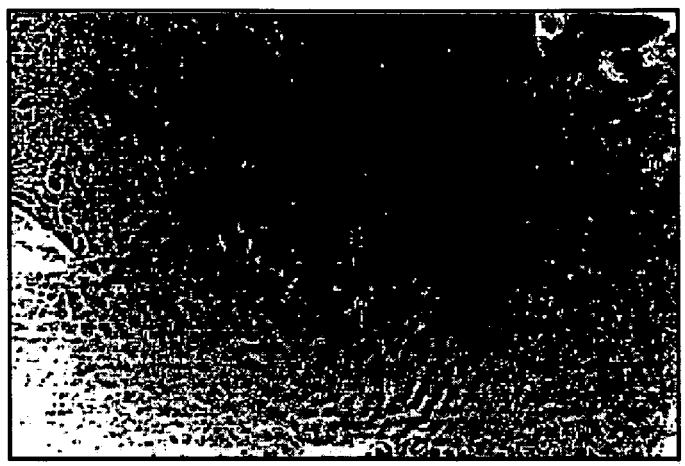
FIG. 1(C) monolayer growth of Evans undifferentiated cells (FIG. 5B, Evans); versus FIG. 1(D) multilayered growth of the "embryonic stem cells" from an established cell line of the present invention at 200× magnification.
Figure 1D:
FIG. 1 (includes FIGS. 1A, 1B, 1C and 1D) is a comparison of morphological characteristics of development of cells designated "stem cells" by Evans (top panel) and the "embryonic stem cells of the present invention" using swine cells (bottom panel).

Transgenic animals possess an alteration in their DNA which has been stably incorporated into the genome as a result of intentional experimental intervention. In the present method, a cell or cells from an ungulate embryonic stem (ES) cell line are introduced into a host embryo to create a chimeric animal. A certain percentage of these animals are germ cell chimeras, but this is not required to define an "ES-cell," because morphological and biochemical characteristics as well as the ability to create different transgenic chimeras, must also be considered. (In mammals, germ cells segregate from somatic cells at the early primitive streak stage. Transformation of a cell occurring after that time results either in a transformed germ cell or a transformed somatic cell.)

When ES cells are introduced into an embryo, the distribution of ES cell descendents in the various tissues of the resulting chimera depends on the ratio of ES/embryonic cells at the time of ES cell introduction, the position of the ES cells in the embryo, and chance. Although coat color chimerism is an easily detectable manifestation of chimerism, an animal that doesn't exhibit coat color chimerism could be a germ cell chimeric, and so forth.

Transgenic lines are produced by breeding the chimeric animals and by selecting offspring of the breeding that exhibit transgenic expression. These offspring are sometimes referred to as "germline transgenics." An alternative method to produce transgenic animals is to transfer nuclei from the ES-cell line into a cell from which an embryo develops.

Among the advantages of using embryonic stem cells to produce chimeric and transgenic ungulates, are that efficiency is improved, and that transformed ES-cells can be used as the progenitors of clonal lines (descendent lines having the same genotype as the single parental cell, barring mutation). These clonal lines are manipulated to alter the genetic complement of their cells. Large numbers of the altered cells may be replicated in vitro so that replicate animals may be produced.

A significant advantage of the present invention is the ability to control and reproduce genetic manipulation by using cultured ES cells as the vehicles for the manipulation. Introduction of transgenes to specific chromosomal locations is referred to as "gene targeting" because it allows the reproducible incorporation of a nucleotide sequence into a specific location of the host genome. Such targeting can result in the gene knockouts and gene replacements referred to above.

The strategy of creating animals with specific genetic changes has immense potential use in agriculture. This use includes producing plants and animals with new, improved genomes. These improvements may be in the plant or animal itself, such as reduced spoilage or better taste, or may be in new uses for the transformed plant or animal, for example as a factory to produce pharmaceuticals, or as a production line for organs used in human transplants. The methods and compositions of the present invention bring these strategies into actuality for ungulates.

Versatility in the kinds of genetic manipulation possible in embryonic stem cell cultures, reproducibility of the methods to make such cultures, and predictability of results of genetic manipulation are other advantageous aspects of the present invention.

An initial step in the method is to establish a stable, undifferentiated embryonic stem (ES) cell line. For purposes of the present invention, stable means maintaining essentially similar cell types and growth parameters through serial subcultures, under the same environmental conditions, and maintaining a stable, modal chromosome complement. "Modal" refers to the most frequent chromosomal count per cell. "Stable" in reference to a chromosomal complement refers to maintenance of the same modal number cell and culture morphology over repeated subculture. "Undifferentiated" in this context means not showing morphological or biochemical evidence of differentiation. An embryonic stem cell is an undifferentiated cell which is capable of differentiating into embryonic structures. An embryonic stem cell line is derived from a culture of embryonic stem cells. Because ES-cells may differentiate, and because a culture may include both differentiated and undifferentiated cells (the latter defined as the ES-cells of the present invention) a culture is defined to be stable if at least 50%, preferably 70–80% of the cells are ES-cells.

A preliminary step in isolating embryonic stem cells is to collect embryos. The pattern of development during cleavage is similar for ungulates in the Order *Artiodactylia* (swine, cattle, sheep, goats) (Bearden and Fuquay, 1980). The stages of development from zygote to blastocyst are essentially identical for these species, therefore similar criteria apply for collection of embryos to generate ES-cells. It is likely that the more cells in the inner cell mass (ICM), the better the chance of making a cell line. After formation of the blastocyst and subsequent hatching from the zona pellucida, the embryos begin to elongate (Cruz and Pedersen, 1991). This elongation occurs on day 11 post-estrus in the pig, sheep and goat, and on day 13 in the cow (Bazer, Geisert, Zavy, 1987). This is further evidence supporting the similarity of the pre-implantation embryo development in these species (pig, cow, sheep, goat). This elongation stage also marks a point at which embryos have passed beyond a stage suitable to be selected for producing ES-cells.

In an illustrative embodiment using pigs, females are checked for estrus, preferably twice daily. Donor sows for the ES-cells are inseminated at the time of the female pig's estrus. Embryos are then collected on days 1.5–5.5 post estrus if the pre-blastocyst stage is sought, on days 5.5–7.5 post estrus if expanded blastocysts are desired, or on days 7.5–10.0 post estrus if hatched blastocysts are sought. Both morphological criteria as defined herein, and day of the development are used to select embryos.

An expanded blastocyst is defined herein as a stage of embryo development in which the embryo has a blastocoel (fluid filled cavity) with an inner cell mass (ICM) and trophoblast which has flattened out and expanded within the zona pellucida has expanded in diameter.

Embryo cultures are initiated using suitable media, culture dishes, temperature, and other conditions. In an illustrative embodiment, embryos are grown on or with feeder layers of cells in SCM mediums. Modified Whitten's or modified BECM medium may be used to wash the embryos, and as an alternative to stem cell medium (SCM) for culture to hatching. BECM is only used for washing and short term (<6–8 hrs.) cultures. After about 24–48 hours in culture, expanded blastocysts generally hatch from the zona pellucida and attach to the substrate. Alternatively, hatched blastocysts attach to the culture dish after about 24–48 hours in culture (range 1–10 days).

Embryonic stem cells are isolated from the attached embryos and maintained in cultures. The inner cell mass (ICM) of the cultured embryo is evident during the first 1–14 days of culture. After the ICM emerges, it is dislodged from the culture dish, and its cells are disaggregated, generally by a combination of proteolytic enzymes and mechanical agitation.

The disaggregated cells are cultured until nests of round cells appear, generally after 7–8 days (range ~2–21 days) in culture. Conditioned stem cell medium in the absence of a feeder layer is suitable for this growth stage. However, use of feeder layers is preferred.

Initial attachment of the hatched porcine and sheep blastocyst to the feeder layer or culture vessel (in conditioned stem cell media (CSCM)) is different from the mouse blastocyst. In the mouse, the hatched blastocyst (HB) plates down and attaches with the inner cell mass (ICM) growing up like a hilus or polyp. The trophoblast cells grow outward from the ICM, leaving a clear zone between the ICM and the trophoblast cells. This configuration allows for easy "plucking" of the ICM, essentially free of trophoblast cell contamination. The isolated ICM can then be put in trypsin to dissociate the cells for further subculture. "Plucking" is defined herein as manually extracting a cell or a group of cells from a culture. Extraction is by means known to those of skill in the art, for example, by means of a needle, glass pipette, or fine forceps.

On the other hand, in an illustrative embodiment of an ungulate, the pig and sheep HB attaches and plates down in a large clump and then begins to spread out as if it were melting. Consequently, the ICM is associated with trophoblast cells, and its configuration resembles a fried egg in appearance. This phenomenon makes it difficult initially (first several days, 1–5) to pluck the ICM alone, and as a result, depending on the plated configuration of the individual embryo, the ICM may be plucked or the entire plated embryo may be trypsinized to dissociate the cells. After discrete multilayered clumps or colonies of ES-cells are visible, then plucking is done to isolate these cells from contaminating trophoblast and/or other differentiated cell types. This results in purification of cells with the proper ES morphology.

Serial subculture is performed at intervals that are a function of culture growth rate. In an illustrative embodiment, subculture intervals are from 2–14 days (range 1–21 days). As with embryo cultures, feeder cell layers may be used to support growth. Subculturing the culture is continued until a stable culture with morphological features and growth parameters characteristic of an embryonic stem cell culture is established.

In addition to other criteria, the present invention teaches a set of morphologic criteria that provide means for the isolation and propagation of morphologically distinct porcine, bovine, ovine and caprine ES-cells. As a preliminary scan for pluripotency of the ES-cell lines, undifferentiated morphology is sought using the light microscope. Morphologically ES-cells are small (about 8–15 microns in diameter) and rounded, and possess a large dark nuclei which contain one or more prominent nucleoli. The cytoplasmic to nuclear ratio is about 15:85. Scanning electron micrographs of the ES cells reveal a rounded or polygonal cell with close association of cells to one another, irregular surfaces and microvilli evident on the outermost cells of the colony. Culture growth parameters comprise a doubling time of approximately 18–36 hours, and multilayered rather than monolayered growth. Porcine and sheep ES-cells grow in colonies with diameters that range from about 0.08 to 1.5 mm, for example.

In some of the same embryo cultures in which such morphologically distinct ES-cells are found, cells are observed with the distinct morphologic characteristics, hereinafter referred to as the "Evans morphology," that were described as being characteristic of porcine ES-cells by Evans et al. (1981). In accordance with the present invention, cultures predominantly containing cells with the characteristics of the Evans morphology, and not predominantly containing cells with the morphologic characteristics described herein for the cells of the present invention, are discarded. If approximately 50% or more of the cells fit the morphological criteria as defined herein, those cells are selected ("plucked") to enrich for ES-cells in the next subculture. Cells with the Evans morphology, while capable of differentiating to some extent, have never been shown to be capable of generating chimeric pigs.

Established embryonic stem cells grow rapidly, dividing about every 18–36 hours. To protect against spontaneous, unwanted differentiation, cells are generally kept at a high density. Frequent changing of media and subculturing are methods used to maintain healthy cultures of the appropriate density, generally about $1-2 \times 10^6$ cells/100 mm dish which contains about 10–12 ml of medium.

The modal chromosomal count, that is, the most frequent class of the number of chromosomes characteristic of the euploid genome, is evidence for a stable culture. For pigs, the modal number is 38; for cattle 60; sheep 54 and for goats 60.

A preferred method for identifying an embryonic ungulate stem cell culture suitable for incorporation into a host embryo, include the following steps:
 (a) introducing a first embryonic stem cell from culture into an immunodeficient mammal;
 (b) determining if a tumor forms in the mammal from the embryonic stem cell; and if so,
 (c) designating the culture as an "ES" cell culture.

Lack of differentiation as an indicator of an ES-cell may also be determined by absence of cytoskeletal structural proteins such as cytokeratin 18 and vimetin, which are only expressed in differentiated cell types. Conversely, ability of the cells to differentiate after induction, is detected by loss of typical undifferentiated ES-cell morphology and positive fluorescent antibody staining for, e.g., anticytokeratin.

Embryonic stem cells are intrinsically different from typical cultured mammalian cells in that they are highly prone to differentiation, and are thus phenotypically unstable per se. ES-cell cultures thus generally appear in culture as heterogeneous mixtures of ES-cells and non-ES-cells, such non-ES-cells, variously including partially and fully differentiated derivatives of ES-cells and other embryonic cells.

The ES-cells in such cultures are typically seen to grow as clumps of cells with a distinct morphology. The clumps are interspersed with non-ES-cells, which exhibit heterogeneous morphologic characteristics. Useful ES-cell cultures have a low enough percentage preferably 10–30% of such non-ES-cells to enable the isolation of quantities of relatively homogenous ES-cells by the means disclosed herein.

The phenotypic instability of cultured ES-cells results in the continuous alteration of the characteristics of growing ES-cell cultures. Thus, the ES-cell culture requires that the cell culturist frequently, usually daily, evaluate the cells of each culture on a morphological basis, to discard those cultures that contain enough cells that have differentiated to yield a large percentage of non-ES-cells. ES-cell culture involves the cryogenic preservation (freezing) of ES-cells from useful cultures to enable the recovery of the appropriate cells when such cultures inevitably alter their characteristics and lose those characteristics that make them useful.

When ES-cells are first prepared from embryos in culture the heterogeneity that is seen in ES-cell cultures is present to the greatest extent compared to later subcultures. Thus, for the isolation and preparation of ES-cells, many embryos are cultured and only those few that contain large, identifiable aggregate (clumps) of cells with the desired morphologic characteristics are used, while the majority of the cultured embryos are discarded. Thus, the morphologic criteria used to select useful ES-cell cultures for continued propagation are also essential to the initial isolation of ES-cells from embryos and to their expansion into useful ES-cell cultures.

Using methods disclosed herein, ES-cells were developed from Meishan, Yorkshire and Duroc swine and from sheep. Efficiency of producing ES-cells is somewhat affected by strain or breed of donor. Other suitable breeds or types of swine include the NIH mini-pigs, feral pigs, SLA haplotyped swine, and the like.

Transformation of an embryonic stem cell in vitro with a first genetic complement which includes a nucleotide sequence is accomplished by any of the methods known to those of skill in the art. Examples of said methods include electroporation, calcium phosphate precipitation, polybrene precipitation, transduction (retrovirus), receptor mediated DNA transfer, lipofection, microinjection, or other means.

In an illustrative embodiment, a genetic mutation created in vitro is incorporated into a specific site of a host cell genome. If the transformed host cell is a pluripotent or totipotent embryonic stem cell, and said stem cell is incorporated into a chimeric ungulate, a transgenic animal is produced with a specific genetic change in a specific location of the host genome. A requirement for proceeding from a chimera to a transgenic animal, is that a gamete exists which is a descendant of an embryonic stem cell, and that gamete is used to produce an offspring of the chimera. Existence of stable cell cultures allows development of a clone of ES-cells with the same altered genetic complement, therefore, the opportunity arises to replicate transgenic ungulates with the same genetic complement.

Individual cell lines are readily screened to detect homologous or non-homologous recombination of exogenous DNA into chromosomal DNA. Using cell lines produced by the methods of the present invention, transgenic ungulates with a transgene in a specific chromosomal location are produced. Stable, genetically altered lines of transgenic ungulates are readily produced by introducing specific genes at specific locations. Homologous recombination is used to produce gene knockouts or gene replacements as described above as well as to integrate single genes in specific locations, avoiding the introduction of multiple copies of genes, and unpredictable numbers and locations of copies, which have caused problems in previous methods to produce transgenic animals. Insertion of single copies of genes circumvents some of the problems arising from integration of multiple copies as observed when growth hormone genes were introduced into transgenic ungulates produced by other methods.

A method for producing a chimeric ungulate includes an initial step of introducing an embryonic stem (ES) cell which preferably is totipotent and that has a first genetic complement, into a recipient embryo which has a second genetic complement, to make a chimeric embryo.

A nucleotide sequence of the first genetic complement is obtained by isolation from genomic DNA, preparation from cDNA, by direct synthesis, by recombinant techniques, or a combination thereof. Appropriate regulatory sequences are included.

The transforming first genetic complement, for example, an isolated nucleotide sequence, is selected according to a particular goal or goals of producing a transgenic ungulate. Limitations on transformation are those limitations generally known to those of skill in the art. The first complement may be different from the second. The first genetic complement could be a nucleotide sequence which is foreign (exogenous) to the species of the host (recipient), or it could be natural to the host species. In the latter case, the nucleotide sequence could be altered from that naturally present in the host.

An exogenous nucleotide sequence which is desirable to use as a first genetic complement which is incorporated into chimeras, and subsequently into transgenic ungulates, includes genes encoding:
1) blood clotting factors such as Factor VIII and IX;
2) TNFα which is useful for inhibition of adipocytes;
3) growth factors such as
   a) EGF, which is useful for recovery of gastrointestinal linings disrupted after neonatal diarrhea;
   b) NGF, the neural growth factor;
4) iron-binding lactoferrin;
5) hemoglobin for artificial blood or treatment of anemia;
6) hormones such as insulin, FSHβ, GH, LHβ, PMSG; and
7) genes designated as
   a) SLA or MHC which are associated with disease resistance;
   b) cytokine genes;
   c) complement genes.

Angiogenic factors, pharmaceutical or diagnostic proteins, and antibodies are other useful products that may be manufactured by transgenic ungulates, for example, in their milk.

After selecting a suitable embryonic cell, which may be transformed, it is introduced into a recipient embryo generally of the same species, at the desired stage, generally the morula or blastocyst stage. Other stages are also suitable, for example, the one cell, two cell or 8 cell stage. The embryos are then immediately transferred into suitably prepared recipient mothers, or held in culture for up to about 10 days. (Polge, 1982; Webel et al., 1970).

Any method for introducing the cell into the host embryo is suitable, including microinjection. If the introduction is successful, a chimeric ungulate is produced. The chimerism is detected by an assay suitable to detect the gene that was introduced via the transformed embryonic stem cell, usually by detecting an expression product or by means of hybridizing to an identifying probe.

Two methods are used for identifying chimeric offspring. Coat color markers offer a visually observable system for distinguishing chimerism. DNA markers are detectable by analysis of tissue samples. For example, a skin pigment gene not present in the host blastocyst genome, may be detected as spots in the animal.

Informative genetic markers used to screen chimeric animals include polymorphism in the glucose phosphate isomerase (GPI) and the cholesterol-7α-hydroxylase gene systems, microsatellite DNA markers and Y-chromosome specific probes.

The detection of both coat color and DNA chimerism may not be possible in all truly chimeric individuals. Some individuals may not exhibit coat color chimerism but show DNA chimerism. Other individuals may exhibit coat color chimerism but have a very low or zero percentage of DNA chimerism in the blood or other specific tissues. Finally, some individuals which are chimeric at birth may lose cells or tissues derived from the ES cells with increasing age due to ploidy problems with the ES cell lines. (Sims and First, 1993).

The chimeric embryo is placed into an environment suitable for the completion of development to form a chimeric adult, and the chimeric embryo is developed to sexual maturity. An ungulate that is produced from the embryo into which the transformed embryonic cell has been introduced is a presumed chimera. Of course, not all animals so produced are actually chimeric due to technical variation and chance. However, for pigs the success rate per embryo is higher (~30%, range 25–100%) than reported by others attempting to produce transgenic pigs using microinjection.

The chimeric animal may be bred to produce an offspring. It is preferable to determine whether the offspring is a transgenic ungulate by detecting the first genetic complement (a transgene) in the offspring, either by detecting its expression product, or its specific nucleotide sequence. Genetic markers are useful to trace descent of the transgene.

Swine are generally of the genus and species *Sus scrofa*. In an illustrative embodiment, the chimera comprises embryonic stem cells from a first breed of swine, for example, the Meishan line and a morula from a second breed of swine, for example, the Duroc line.

In the goat, *Capra hircus*, a suitable first breed is Saanen, a suitable second breed is Toggenburg. In sheep, *Ovis aries*, a suitable first breed is Dorset, a suitable second breed is Lincoln (homozygous black strain). In cattle *Bos taurus*, a suitable first is Angus and a suitable second breed is Hereford.

Chimeras are preferably designed so that they could be easily screened using coat color markers (i.e., Meishan X Duroc, for pigs, Angus X Hereford for cattle, Dorset X Lincoln (homozygous black strain) for sheep, Saanen X Toggenburg, or Black or Brown Nubian, for goats).

Figure 3A:
FIG. 3A is a photograph of a chimeric pig showing a varied coat color pattern. Coat color patterns varied between individuals but included single or multiple areas of black hair (arrows), dorsal and ventral striping or a combination of these patterns.
Figure 3B:
FIG. 3B is a photograph of a chimeric pig (center) between a purebred Duroc pig (left, the breed of recipient embryo) and a purebred Meishan pig (right, breed of ES-cell line).
Figure 3C:
FIG. 3C is a photograph of the chimeric pig designated C019.

Chimeric pig embryos were produced using two coat color markers: Meishan (black hair with black skin pigmentation) ES-cells were injected into Duroc (red-brown hair with pink skin pigmentation) embryos. These combinations allowed for easy visual detection of chimeric animals. (FIG. 3)

At birth, coat color chimerism was observed in 22 of the 48 piglets born (Table 1). Individual coat color patterns varied but included single or multiple areas of black spotting of skin and hair, dorsal and ventral striping or a combination of these patterns (FIG. 3). Similar coat color patterns have been previously reported for chimeric mice. (Mintz, 1967) Microscopic examination indicated chimerism may extend to the individual hair follicles in the mouse. (McLaren and Bowman, 1969)

TABLE 1

Production of Porcine Chimeras by Microinjection of Meishan Embryonic Stem Cells

| ES Cell Line[a] | Embryos Injected | Embryos Transferred | No. Live Born Pigs (%) | Coat Color Chimeras[b] | Blood Cell Chimerism[c] |
|---|---|---|---|---|---|
| M175F(16) | 75 | 72 | 29(40.3) | 21 | ? ND[d] |
| M688(12) | 74 | 74 | 16(21.6) | 0 | No |
| M1192(10) | 74 | 64 | 3(4.8) | 1 | Yes |
| TOTAL | 233 | 210 | 48(22.8) | 22 | |

[a]Numbers in parentheses is the passage number of the ES cell line.
[b]Coat color chimerism was determined at birth. In the reference swine herd, at the University of Illinois for the past 15 years (in 1993 the University of Illinois was the 10th largest pure-bred Duroc breeder in the USA) no individuals of the purebred Duroc genotype were observed with the present phenotype at birth. In the referenced herd 1500–2000 pure bred Durocs were born per year. For pure-bred registration all animals mustbe inspected all over for color, conformation and type. Red color is recessive so all other colors would show-up in the offspring if present.
[c]Chimerism in blood was determined using breed and/or sex specific DNA markers.
[d]DNA chimerism has not yet been established for all coat color chimeric individuals with this cell line (ND = not yet determined).

The presumed chimeric ungulates are then bred to produce offspring. Some of the chimeric animals used as parents a transformed gamete. If a transformed gamete is used in fertilization, the resulting offspring is a transgenic animal, because all of its cells are descended from the zygote formed by the transformed gamete, therefore, all of the offspring's cells are expected to be transgenic. Of course, not all the offspring of chimeric ungulates are transgenic, because not all chimeric ungulates have transformed gametes, or have all of their gametes transformed.

To produce a transgenic animal, the genetic complement, for example, an isolated nucleotide sequence initially used to transform an embryonic stem cell of the present invention, must be incorporated into the genome of the host. If the transforming nucleotide sequence includes exogenous DNA, which is generally the case, the exogenous DNA must become incorporated into the endogenous DNA of the host. Incorporation is generally accomplished by non-homologous recombination. However, homologous recombination may also be the means for achieving DNA incorporation. Homologous recombination is defined herein as recombination between related or identical DNA sequences; non-homologous recombination as recombination between unrelated DNA sequences.

Transgenic ungulates with altered tissue or milk proteins or compounds produced as a result of protein production, include pharmaceutical, therapeutic, biomedical, processing, manufacturing or compositional proteins such as the following:

1) blood proteins (clotting factors VIII and IX, complement factors or components, hemaglobins or other blood proteins and the like;
2) hormones (insulin, growth hormone, thyroid hormone, catecholamines gonadotrophins, PMSG, trophic hormones, prolactin, oxytocin, dopamine and the like);
3) growth factors, i.e., EGF, PDGF, NGF, IGF's and the like;
4) cytokines, i.e., interleukins, CSF, GMCSF, TNF, TGFα and β and the like;
5) enzymes (tissue plasminogen activator, streptokinase, cholesterol biosynthetic or degradative, digestive, steroidogenic, kinases, phosphodiesterases, methylases, de-methylases, dehydrogenases, cellulases, proteases, glycosolases, lipases, phospholipases, aromatase, cytochromes, adenylate or guanylate cyclases and the like);
6) hormone or other receptors (LDL, HDL, steroid, protein, peptide, lipid or prostaglandin and the like);
7) binding proteins (steroid binding proteins, growth hormone or growth factor binding proteins and the like);
8) immune system proteins (antibodies, SLA or MHC genes);
9) antigens (bacterial, parasitic, viral, allergens and the like);
10) translation or transcription factors, onco-proteins or proto-oncoproteins, milk proteins (caseins, lactalbumins, whey and the like); and
11) muscle proteins (myosin, tropomyosin and the like).

An aspect of the present invention is a system to screen embryonic cells for transgene expression prior to production of transgenic animals. In this assay, ES-cells introduced into SCID mice (or other immune deficient or immuno-compromised rodents) produce tumors. These may be teratomas or teratocarcinomas, comprised of a number of fully differentiated tissues (including: muscle, bone, fat, cartilage, skin, epithelia, nervous, glandular, hemapoetic, secretory and the like). Each line of transgene-carrying ES-cells can be injected into SCID (or other immune deficient or immuno-compromised mice) and the tumors harvested. In situ hybridization, immunocytochemistry, solution hybridization, Northern, Southern or Western analysis or the like can then be performed to determine which tissue types express the transgene. This methodology is useful for the rejection of transformed ES lines in which proper expression of the transgene did not occur. Further, this method presents a short cut to chimera or transgenic animal production in gene regulation studies.

The following protocols and procedures are embodiments of various aspects of the invention. Formulation of various media, solutions and the like, are found in the Materials and Methods section.

1. Purification of Undifferentiated Embryonic Stem (ES) Cell Lines

Step 1:

Isolated, individual porcine, bovine, ovine or caprine embryos allowed to develop either in vivo or in vitro and allowed to escape from the zona pellucida either by natural hatching, mechanical or chemical removal are initially cultured on either (1) feeder layers including mitomycin C-inactivated mouse embryonic fibroblast (STO) monolayers or another cell layer such as mouse primary embryonic fibroblasts (PEF) or ungulate primary embryonic fibroblasts, with ES culture medium (SCM) which consisted of Dulbecco's Modified Eagle's Medium with only Fetal Calf Serum (20%), β-mercaptoethanol, antibiotics, nucleosides and non-essential amino acids, or (2) in conditioned stem cell medium (CSCM) which consisted of ~40% Dulbecco's Modified Eagle's Medium (DMEM) and ~60% Buffalo Rat Liver cell conditioned medium (BRL-CM) containing a total of approximately 20% fetal calf serum (FCS), β-mercaptoethanol, antibiotics, nucleosides and non-essential amino acids (Smith and Hooper, 1987).

Step 2:

After about 4–21 days the colonies are (1) plucked, that is, removed selectively from a dish, or (2) the whole dish may be dispersed with trypsin and plated onto plates containing only conditioned medium (treatment 1), or plated onto STO feeder layers (treatment 2), as disclosed herein. PROTOCOL: ES-cell colonies are dislodged from the underlying cells and washed through two changes of calcium/magnesium-free PBS. The colonies are then transferred to drops of trypsin solution (0.25% trypsin, 0.4% EDTA in Ca++, Mg++-free phosphate buffered saline, PBS; and incubated for 1–5 min at 37–39° C. Alternatively, the entire dish of cells may be washed and trypsinized. The cells are disaggregated by vigorous pipetting with a fine bore Pasteur pipette. The cells are placed in 1 ml of conditioned stem cell medium (CSCM) to neutralize the trypsin. CSCM is comprised of ~40%. Dulbecco's Modified Eagle's Medium (DMEM) and ~60% Buffalo Rat Liver cell conditioned medium (BRL-CM) containing a total of approximately 20% fetal calf serum (FCS), β-mercaptoethanol, antibiotics, nucleosides and non-essential amino acids (Smith and Hooper, 1987). ES-cells in both treatments were allowed to grow in the culture.

Step 3:

After an additional 2–21 days the colonies again are either plucked (treatment 1) or the whole dish (treatment 2) is placed onto plates containing only conditioned medium. ES-cells in both treatments are allowed to grow in culture. Feeder layers may also be used to support growth. Either SCM or CSCM may be used in the presence of a feeder layer.

PROTOCOL: as above in step 2.

Step 4:

After an additional 2–21 days the colonies are either plucked (treatment 1) or the whole dish (treatment 2) is placed onto plates containing only conditioned medium. ES-cells in both treatments are allowed to grow in culture.

PROTOCOL: as above in step 2.

Step 5:

After an additional 2–21 days if there are sufficient cell numbers, approximately $5–10\times10^6$ cells, then part of the cells are subcultured and part are frozen to serve as a back-up stock of these stem cell colonies.

Step 6:

The cells that were cultured in only CSCM (or with feeder cells through step 2) are passed every 2–4 days in only CSCM, until ES-cell lines with consistent morphology, i.e. size 8–15l, with a nuclear to cytoplasmic ratio of ~85:15, and colony growth characteristics (doubling time 18–36h) are established. This entire process (Steps 1–6) may take from 5–21 weeks to isolate a single ES-cell line. These lines are then used for production of chimeras and/or nuclear transfer. It is then determined whether the proper cells have been isolated at this point of the procedure. (see step 7, following)

Serial subculture is performed at intervals that are a function of growth rate. In an illustrative embodiment, subculture intervals are from 2–14 days (range 1–21 days). As with embryo cultures, feeder cell layers may be used to support growth. Subculturing is continued until a stable culture with morphological features and growth parameters characteristic of an embryonic stem cell culture is established.

Embryonic stem cells are intrinsically different from typical cultured mammalian cells in that they are highly prone to differentiation, and are thus phenotypically unstable per se. ES-cell cultures thus generally appear in culture as heterogeneous mixtures of ES-cells and non-ES-cells, such non-ES-cells, variously including partially and fully differentiated derivatives of ES-cells and other embryonic cells.

The ES-cells in such cultures are typically seen to grow as clumps of cells with a distinct morphology. The clumps are interspersed with non-ES-cells, which exhibit heterogeneous morphologic characteristics. Useful ES-cell cultures have a low enough percentage preferably 10–30% of such non-ES-cells to enable the isolation of quantities of relatively homogenous ES-cells by the means disclosed herein.

The phenotypic instability of cultured ES-cells results in the continuous alteration of the characteristics of growing ES-cell cultures. Thus, the ES-cell culture requires that the cell culturist frequently, usually daily, evaluate the cells of each culture for morphological changes, to discard those cultures that contain too many cells that have differentiated thereby yielding a large percentage of non-ES-cells.

ES-cell culture involves the cryogenic preservation (freezing) of ES-cells from useful cultures to enable the recovery of the appropriate cells when such cultures inevitably alter their characteristics and lose those characteristics that make them useful.

When ES-cells are first prepared from embryos in culture the heterogeneity that is seen in ES-cell cultures is present to the greatest extent compared to later subcultures. Thus, for the isolation and preparation of ES-cells, many embryos are cultured and only those few that contain large, identifiable aggregate (clumps) of cells with the desired morphologic characteristics are used, while the majority of the cultured embryos are discarded. Thus, the morphologic criteria used to select useful ES-cell cultures for continued propagation are also essential to the initial isolation of ES-cells from embryos and to their expansion into useful ES-cell cultures.

In addition to other criteria, the present invention teaches a set of morphologic criteria that provide means for the isolation and propagation of morphologically distinct porcine, bovine, ovine and caprine ES-cells. As a preliminary scan for pluripotency of the ES-cell lines, undifferentiated morphology is sought using the light microscope. Morphologically ES-cells are small (about 8–15 microns in diameter) and rounded, and posses large dark nuclei which contain one or more prominent nucleoli. The cytoplasmic to nuclear ratio is about 15:85, and the growth parameters comprise a doubling time of approximately 18–36 hours and multilayered rather than monolayered growth. In some of the same embryo cultures in which such morphologically distinct ES-cells are found, cells are observed with the distinct morphologic characteristics, hereinafter referred to as the "Evans morphology," that were described as being characteristic of porcine ES-cells by Evans et al. In accordance with the present invention, cultures predominantly containing cells with the characteristics of the Evans morphology, and not predominantly containing cells with the morphologic characteristics described herein for the cells of the present invention, are discarded. If approximately 50% or more of the cells fit the morphological criteria as defined herein, those cells are selected ("plucked") to enrich for ES-cells in the next subculture. Cells with the Evans morphology, while capable of differentiating to some extent, have never been shown to be capable of generating chimeric pigs.

Step 7:

This step in the isolation procedure involves injection of the ES-cells underneath the tunica albuginea of the testis of immune system compromised rodents (e.g. SCID, irradiated nude mouse or rat) to produce teratocarcinomas. The mice are examined for the presence of tumors daily. When palpable tumors are observed the rodent is euthanized and the tumor harvested. Undifferentiated ES-cells are recovered from the tumor and re-introduced into in vitro culture to check whether their morphology and growth characteristics match those expected of ES-cells. ES-cell lines with appropriate morphology, size 8–15μ, with a nuclear to cytoplasmic ratio of ~85:15, and growth characteristics (doubling time of 18–36 h) are re-established in culture and selected as in Step 6. These lines are used for production of chimeras and/or nuclear transfer. Alternatively, cells from cultures that test positive in the teratocarcinoma assay of step 7, are used.

NOTE: This step may occur at any point where ES-cells of proper morphology are observed.

Step 8:

Periodically it is necessary to pluck colonies as outlined above and re-isolate the ES-cells with consistent morphology, size 8–15μ, with a nuclear to cytoplasmic ratio of ~85:15, and growth characteristics (doubling time of 18–36 h).

NOTE: Maintenance of these isolated, purified undifferentiated ES-cell lines is required to insure the proper cell type for generation of chimeras and for nuclear transfer. Some differentiation occurs spontaneously during in vitro culture and as a result of the freezing process. These differentiated cells do not subculture well, and occasionally it is necessary to re-purify the ES-cells from the differentiated cells.

Step 9:

To obtain enriched populations of ES-cells (size 8–15μ with a nuclear to cytoplasmic ratio of ~85:15, and doubling time of 18–36 h) for chimera production or nuclear transfer, ES-cell colonies are dislodged from the underlying cells and washed through two changes of calcium/magnesium-free PBS. The colonies are then transferred to 50 μl drops of trypsin solution and incubated for 1–5 min at 37–39° C. The colonies are placed in 1 ml of conditioned stem cell medium (CSCM) to neutralize the trypsin. The cells are disaggregated by vigorous pipetting with a fine bore Pasteur pipette.

Purification of porcine, bovine, ovine and caprine ES-cells may also be performed by centrifugal elutriation, flow cytometry, unit gravity sedimentation, differential centrifugation, cell separation, immuno-surgery to preferentially kill mouse cells or differentiated swine cells, plucking of colonies or individual cells, differential or immuno-staining, production of chimeric embryos and re-isolation of inner cell mass and stem cells, affinity chromatography of ES vs. other swine cell types or mouse cells, mobility in electric fields, and the like.

More specifically:

ES-cell colonies are dislodged from the underlying cells on tissue culture plates and washed through two changes of calcium/magnesium-free PBS. The colonies are then transferred to 50 μl drops of trypsin solution (0.25% trypsin, 0.4% EDTA in Ca++, Mg++-free phosphate buffered saline, PBS; 1.0% NaCl, 0.025% KCl, 0.025% $KH_2PO_4$ and 0.114% $Na_2HPO_4$, pH 7.2) and incubated for 1–5 min at 37–39° C. The cells are disaggregated by vigorous pipetting with a fine bore Pasteur pipette. The colonies are placed in 1 ml of conditioned stem cell medium (CSCM) to neutralize the trypsin. CSCM is comprised of ≈40% Dulbecco's Modified Eagle's Medium (DMEM) and ≈60% Buffalo Rat Liver cell conditioned medium (BRL-CM) containing a total of ≈20% fetal calf serum (FCS), β-mercaptoethanol, antibiotics, nucleosides and non-essential amino acids (Smith and Hooper, 1987). The cells are pelleted by gentle centrifugation and either; 1) left at room temperature overnight followed by subculture onto new petri plates with CSCM, 2) left at room temperature overnight followed by subcultured onto new petri plates with fresh mitomycin C-tested STO Feeder Layers and CSCM or 3) immediately subculture onto new petri plates with CSCM or 2) immediately subcultured onto new petri plates with fresh CSCM.

TABLE 2

COMPARISON OF METHODS OF MAKING EMBRYONIC STEM CELL LINES

|  | Mice | Evans | Pied.[b] | Pig[c] | Cattle[c] | Sheep[c] | Goats[c] |
|---|---|---|---|---|---|---|---|
| Embryo Stage | 3.5 d | 6.5–11 d | 7–8 d | 6.5–10 d | 5–9 d | 6–7 d | 5–7 d |
| Medium Additives | DMEM BME neaa nucleosides | DMEM .1% BME neaa — | DMEM BME — — | DMEM BME neaa nucleosides | DMEM BME neaa nucleosides | DMEM BME neaa nucleosides | DMEM BME neaa nucleosides |

TABLE 2-continued

COMPARISON OF METHODS OF MAKING
EMBRYONIC STEM CELL LINES

| | Mice | Evans | Pied.[b] | Pig[c] | Cattle[c] | Sheep[c] | Goats[c] |
|---|---|---|---|---|---|---|---|
| Serum | 10% FBS | 10% FBS | 10% FBS | 18–20% FBS | 18–20% FBS | 18–20% FBS | 18–20% FBS |
| | 10% newborn calf | 10% newborn calf | 10% Calf Serum | | | | |
| Feeder Layer Isolation of ICM | STO | STO | STO or HEF & Immuno Surgery | STO or only conditioned medium (CSCM) | STO or only conditioned medium (CSCM) | STO or only conditioned medium (CSCM) | STO or only conditioned medium (CSCM) |
| Feeder Layer Maintenance of lines | STO | STO | STO OR HEF | Conditioned (CSCM) media | Conditioned (CSCM) media | Conditioned (CSCM) media | Conditioned (CSCM) media |
| Purified | no | no | no | yes | yes | yes | yes |

[a]Manual hatching is disclosed, but it is not clear if all treated blasts are hatched.
[b]Pied. = Piedrahita et al. 1990a and b.
[c]Present invention.

2. In Vitro Characterization of ES-Cell Lines

An aspect of the invention is to select a transformed embryonic stem cell in vitro which is likely to produce a chimeric state when introduced into an ungulate embryo. The selection criteria are based on morphological characteristics of the transformed embryonic stem cell. Generally, morphological characteristics identifiable by inspection of the cell using the light microscope are predictive, although other assays for predictive morphological characteristics are also within the scope of the present invention.

Figure 2:
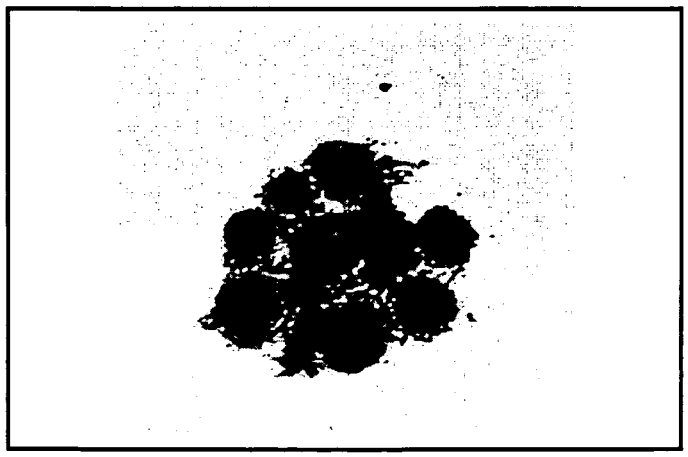
FIG. 2 is a photograph of ES-cells of the present invention stained with Giemsa at 400×; cells are dispersed and fixed on slides.

In culture, embryonic stem cells of the present invention are translucent, and grow in clumps. Cells will cover the entire culture surface eventually, and tend to form colonies or nests (clumps) of multilayers as opposed to monolayer growth. (FIGS. 1, 2). In a culture of embryonic stem cells, some will remain undifferentiated, others will differentiate, that is will start to show structures and markers reminiscent of organized tissues e.g. renal tissue. Differentiated cells have light refractory or round or polygonal cell borders. The cells will also form fluid filled domes with cells exhibiting the currently described ES morphology. The doubling rate of these cells is about 18–36 hours. These characteristics differ little from those reported for mouse embryonic stem cells, but do differ significantly from those reported by Evans. (FIG. 1, Table 2).

Diameter of the colonies ranged from 0.08 to 1.5 mm four days after plating as a single cell suspension. Porcine ES cells are small (8–12 μm diameter), rounded and dark, yet translucent. The nucleus contains several prominent nucleoli and makes up ~80% of the cell volume. Scanning electron micrographs have shown the close association of the cells with each other obscuring the cellular boundaries. The surface of the colony is irregular as is the surface of individual cells. Microvilli were evident on outermost cells. The average doubling time of the pig ES cells is 18–36 hr after passages 5–7 and is relatively constant thereafter.

The overall efficiency of producing ES cell lines from porcine blastocysts is low. A total of 1524 blastocysts were collected and cultured. The number of these embryos that survived to passage 1 was 490 (32.1%). The number of embryos surviving to passages 4–6 was 104 (21.2% of embryos passed, 6.8% overall). Twenty-one percent (22/104, 1.5% overall) of the presumptive ES cell lines that reached passage 4, retained the morphological and growth characteristics indicative of pig ES cells. Three of these lines were tested to produce chimeric pigs. There are significant breed as well as individual donor differences in producing ES cell-like colonies.

Similarities of individual ungulate (embodied as swine) ES-cells to mouse embryonic stem cells include that the nucleus to cytoplasmic ratio is approximately 85:15. The nucleus is round and contains several prominent nucleoli. Cell size varies somewhat among isolated lines, but most of the stable lines consist of round cells with diameters in the range of 8–15 microns.

In Table 3 the differences between the purported ES swine cells of Evans, and those of the present invention are set forth. Also, the similarities between the swine cells disclosed herein and the ES-cells of mice are described.

TABLE 3

COMPARISON OF CELL MORPHOLOGY OF
MICE AND OF UNGULATE ES-CELLS

| Parameter | Mice | Evans Swine | Pig[c] | Ungulates[d] |
|---|---|---|---|---|
| Size | 11–12 μm | "larger than those of the mouse" | | 8–15 μm |
| Shape | round | round | round | round |
| Monolayer colonies | no | yes | | no |
| Distinct individual cells can be identified | no | yes | | no |
| Cytoplasm (% of cel vol) | 25% | small | | 10–25% |
| Nucleus (% of cel vol) | 75% | large (no data) | large | 75–90% |
| Number of nucleoli | 2–4 | 2–4 | 2 | 2–4 |
| Teratocarcinoma production in SCID mouse | yes[b] | ? | | yes |

TABLE 3-continued

COMPARISON OF CELL MORPHOLOGY OF
MICE AND OF UNGULATE ES-CELLS

| Parameter | Mice | Evans Swine | Pig[c] | Ungulates[d] |
|---|---|---|---|---|
| State of embryo cultured[e] | 3.5d blastocysts, post coitus | 6.5–11 d hatched blastocysts | | 7.5–10 d hatched blastocysts |

[a]Evans relates "a variety of sizes" (column 10 of Evans patent), and sizes varying among cell lines. Bovine cells are also related.
[b]Wheeler et al. unpublished results.
[c]Piedrahita et al., 1990a, b.
[d] Present invention, from swine
[e]Estrus is day 0 in all species 3. Teratoma/Teratocarcinoma Assay for Ungulate Embryonic Stem Cells As part of the screening process during development of ungulate lines, an assay for determining whether a cell culture included ES-cells, was to introduce cells from the culture into an immunodeficient mammal to see if a tumor formed. Production of a teratoma or a teratocarcinoma is a criterion for inferring that the culture tested included ES-cells. A teratoma is a true neoplasm composed of bizarre and chaotically arranged tissues that are foreign embryologically, as well as histologically, to the area in which the tumor is found. A teratocarcinoma is a teratoma with carcinomatous elements. A carcinoma is a malignant epithelial tumor.

All lines which are truly pluripotent should proliferate, differentiate and form tumors in severe combined immunodeficient mice (SCID) or other immunologically noncompetent animals. Those cell lines which produce tumors are preferable as ES-cells for use in the production of chimeric animals. The selection process is two fold: 1) only the cell lines which were capable of forming tumors are maintained; and 2) only the cells from the tumors or those maintained in number 1), which have maintained their undifferentiated state, are utilized in chimera production.

The following protocol was used for the assay. Cells were introduced into adult male SCID mice anesthetized with tribromoethanol (0.005 g/5 g BW). Testes were exposed through a ventral midline incision. In an illustrative embodiment, approximately 2×10$^6$ cells were injected through a 26 gauge needle under the tunica albuginea of one testicle and the other was injected with media only. For some cell lines, more cells may need to be used. Therefore, a culture should not be assayed as negative until larger numbers of cells are tested. A maximum of about eight weeks of observation should be completed before concluding tumors are not produced.

Three weeks following injection of the cells, animals were euthanized and examined for the presence of tumors. Cells from the tumor were then put into the ES-cell culture system. During 7 days of culture, some swine cells differentiated while others maintained their original embryonic undifferentiated morphology. These undifferentiated colonies were then selected, isolated and grown up for use in the production of chimeras.

4. In Vitro Differentiation of Pluripotent ES-Cells

True ES-cells are induced to differentiate in vitro into ectoderm, mesoderm, and endoderm. There is a concomittant loss during said differentiation of characteristics of undifferentiated ES-cell morphology as described herein for an ungulate, and elsewhere for the mouse.

A method for inducing differentiation in ES-cells is to culture cell lines at high density on feeder layers until the cells form small, free-floating cell aggregates. The aggregates are harvested, dispersed, and replated onto 60 mm tissues culture plates coated with 0.1% gelatin.

The replated aggregates are cultured without the addition of exogenous agents to the media, until cells are confluent. This is accompanied by a high cell density.

The culture media is changed about every 48 hours and cells are examined daily for evidence of differentiation. Generally, about 30–40% of the cells terminally differentiate under these conditions, that is, reach a recognizable cell type according to criteria known to those of skill in the art. The most commonly observed cell type has a fibroblast type of morphology. If the fibroblast cells are not subcultured, they will eventually develop into adipocyte-like cells about 50 microns in diameter.

Complex cellular structures that are tubular in morphology also appear. In monolayer cultures, some cell structures reach 100 microns in length. These network-like structures resemble capillaries and are similar to structures reported in mice. Less commonly, neuronal-like cells also are found in these cultures. The nature of the differentiated cell types is determined by immunofluorescence as described in the methods section herein.

Undifferentiated, pluripotent cells lack the cytoskeletal structural proteins cytokeratin 18 and vimentin, which are only expressed in differentiated cell types. For example, "epithelial-like" cells reported by others test positive for cytokeratin 18. Antibodies are available which are directed against antigenic structures which are indicative of cellular differentiation. (Rudnicki and McBurney, 1987). Examples of these structures include neurofilaments (expressed in ectoderm), glial fibrillar protein (expressed in ectoderm), keratin (expressed in endoderm) and desmin (expressed in mesoderm). Formation of antigen-antibody complexes are indicative of a differentiated state; conversely, absence of an antigen-antibody reaction is evidence for lack of differentiation.

Evidence of pluripotency is provided by differentiation of structures from all the embryonic layers, from a single cell line.

Pluripotent cells lack the cytoskeletal structural proteins, cytokeratin 18 and vimentin, which are only expressed in differentiated cell types. Positive staining against specific antigens, including neurofilaments (expressed in ectoderm), glial fibrillar acidic protein (expressed in ectoderm), keratin (expressed in endoderm) and desmin (expressed in mesoderm), is indicative of cellular differentiation. Replicate colonies of ES-like cells exhibiting undifferentiated morphology were examined for the presence or absence of staining for vimentin, cytokeratin 18, neurofilaments, glial fibrillar acidic protein, keratin and desmin. (Table 4). The cell lines used in the test exhibited morphologies suggestive of ES-cells.

TABLE 4

IMMUNO-STAINING OF
EMBRYONIC CYTOSKELETAL STRUCTURAL PROTEINS

| Antibodies | Cell line MW/D49/ 6-E(T) | Cell line MW/D49/ 6E(C) | Cell line MW/M144- B(T) | Cell line MW/M144- B(C) |
|---|---|---|---|---|
| Control | − | − | − | − |
| FITC$^2$ | − | − | − | − |
| Desmin | + | − | + | − |

TABLE 4-continued

IMMUNO-STAINING OF
EMBRYONIC CYTOSKELETAL STRUCTURAL PROTEINS

| Antibodies | Cell line MW/D49/ 6-E(T) | Cell line MW/D49/ 6E(C) | Cell line MW/M144- B(T) | Cell line MW/M144- B(C) |
|---|---|---|---|---|
| Vimentin | + | − | + | − |
| GFAP[3] | + | − | − | − |
| NF 68,160,200[4] | + | − | + | − |

[1]Letters in parentheses indicate treatment, T = differentiation induced, C = untreated control lines, STO = embryonic fibroblast controls were negative for all antibodies tested;
[2]Fluorescein isothiocyanate control
[3]Glial fibrillary acidic protein
[4]Neurofilament 68kD and 200kD proteins 5. In Vivo Differentiation of Pluripotent ES-Cells; Production of Chimeras.

In vivo differentiation of pluripotent ES cells was tested by their ability to participate in the formation of chimeric offspring. Embryos were collected from Duroc donor gilts 6–7 days after the onset of estrus. These are best for chimeras because they have intact zona pelluciduae s (i.e. not hatched) unlike those hatched blastocysts required for ES cell production.

Duroc morula, blastocyst and expanded blastocyst stage embryos were injected with Meishan ES cells (Table 1). In 210 of 233 embryos, the blastocoel re-expanded following microinjection of ES cells. Embryos which re-expanded were considered to have survived micromanipulation, therefore resulting in a 90% embryo survival rate. These embryos were surgically transferred to recipient gilts and 48 live piglets were born. This represents an overall fetal survival rate of 22.8% (Table 1). The overall pregnancy rate for recipients receiving micromanipulated embryos was 64% (7/11 recipients were pregnant). The group pregnancy rates for recipients receiving embryos containing ES cells from lines M175F, M688, or M1192 were 80%, 66% and 33%, respectively. (Meishan) ES cell colonies were plucked with a fine pipette to dislodge them from the underlying cells. Colonies were disaggregated into a single cell suspension in trypsin/EDTA solution by gentle pipetting. Morula, blastocyst and expanded blastocyst stage embryos had approximately 5 to 10 ES cells (line M1192) micromanipulated into the cell mass (morula) or into the blastocoel cavity (blastocyst and expanded blastocyst) by means of a glass injection needle. After injection, embryos were immediately transferred to recipient gilts which exhibited the onset of estrus 24 hours after the embryo donor.

A high percentage (86%) of recipient embryos which received ES cells survived micromanipulation. The pregnancy rate using micromanipulated embryos was 33%. In one set of transfers, three offspring were born after transfer of 64 micromanipulated embryos. One female piglet (C019) exhibited coat-color chimerism at birth. Deoxyribonucleic acid was isolated from blood and/or tissue of the three potentially chimeric piglets. Chimerism was analyzed and confirmed by polymerase chain reaction amplification of Meishan-associated 120 bp SW16 microsatellite allele and/or of a 192 bp porcine Y-chromosome specific sequence. The marker system used was sensitive enough to detect DNA in ratios of <1:200. Tissues from piglet C019 that tested positive for the Meishan allele included ear, skin from the black spot and blood. These samples were also positive for the Y-chromosome specific sequence although this animal was a phenotypic female. It appears that the blood samples are consistently higher in Meishan DNA than the other tissues sampled.

In an illustrative embodiment, Meishan swine ES-cells (MW/M175F) were injected into Duroc embryos. Duroc swine are characterized as having red hair and pink skin pigmentation. Meishan swine are characterized as having black hair and black skin pigmentation. These easily visible, inherited traits, allow easy visual screening for presumptive chimeras. In this embodiment, black hair and black pigment appear against a red-brown background if a chimera is produced. In the converse embodiment, Duroc ES-cells are injected into Meishan embryos, and red-brown hair and spots would appear on a black hair, black skin background, if a coat color/skin chimera is present (see Table 5).

TABLE 5

PRODUCTION OF PORCINE CHIMERAS BY MICROINJECTION OF
MEISHAN EMBRYONIC STEM CELLS
INTO DUROC RECIPIENT EMBRYOS

| Recipient Breed | No. Embryos Transferred | No. Live Born Piglets | No. Coat Color Chimeras (%) |
|---|---|---|---|
| Duroc | 18 | 11 | 11(100) |
| Duroc | 20 | 5 | 4(80) |
| Meishan | 19 | 9 | 5(55) |
| Meishan | 7 | 4 | 1(25) |

A photograph of a chimeric pig generated using the ES-cells of the invention as described herein, exhibiting coat chimerism, is show in FIG. 3. In addition to screening for chimeras by observation of the skin of the pigs, screening of genetic markers such as those in the haptoglobin, glucose phosphate isomerase (GPI) cholesterol 7-alpha hydroxylase systems, microsatellite DNA markers and Y probes is available. For example, the Meishan breed has only the B type of the GPI polymorphism, whereas the Duroc breed has both the A and B type. Appearance of the A and B type in a Meishan pig, is evidence of chimerism. An example of a chimeric piglet is one exhibiting A and B GPI isotypes. Such a pig was produced by injecting Duroc (D49/6E) ES-cells into Meishan embryos.

The cholesterol-7α-hydroxylase gene is characterized by a Taq I polymorphism at the cholesterol-7α-hydroxylase gene locus in Meishan, Duroc and Yorkshire breeds of swine. The polymorphic bands for the Meishan breed appear at ~2.5 and ~4 kb. The polymorphic bands for the Duroc and Yorkshire breeds appear at ~2.8 kb and ~5.0 kb. The 2.5 and 4 kb alleles are breed specific only for the Meishan breed. The 2.8 and 5.0 kb alleles are breed specific only for the Duroc and Yorkshire breeds. Appearance of 2 bands (one characteristic of the Meishan breed and one characteristic of the Duroc or Yorkshire breeds) or 3 bands in any combination or 4 bands is evidence of chimerism. Restriction fragment length polymorphisms (RFLP's) are analyzed by Southern analysis, phosphoimagery or autoradiography.

Deoxyribonucleic acid (DNA) was isolated from the blood and/or tissue of all potentially chimeric piglets according to the procedures of Miller et al. (1988). Chimerism was evaluated by PCR amplification of each sample with 2 primer pairs. The first primers used were for the microsatellite SW 16 according to the method of Rohrer et al. (1994). The 120 bp SW 16 allele was found to be Meishan-associated.

In the Meishan pigs screened, 5 different allele sizes were identified, that is alleles designated according to base pair size as 164, 134, 130, 122, and 120 bp. Duroc allele sizes are: 168, 138, 132, and 130 bp. Therefore, alleles 120 and 122 are not shared between Meishan and Duroc breeds of swine. This gives an early identifiable marker to determine if there are Meishan cells present in a Duroc/Meishan individual. The 120 bp SW 16 allele is polymorphic and therefore, is not seen in all Meishan pigs. For ES cell line production, the sires and dams of the Meishan embryos were selected so that the resulting ES cell lines contain the 120 bp SW 16 allele. Both Meishan parents were homozygous for the 120 bp allele in this case. The Durocs sires and dams were heterozygous for the 138 and 168 alleles. The second primers utilized in female offspring were for a 192 bp porcine Y-chromosome specific sequence according to the method of Whetstone et al. (1993). As a control for the PCR, primers were used to specifically amplify the porcine α-lactalbumin gene (Bleck, et al. 1994).

Figure 4:
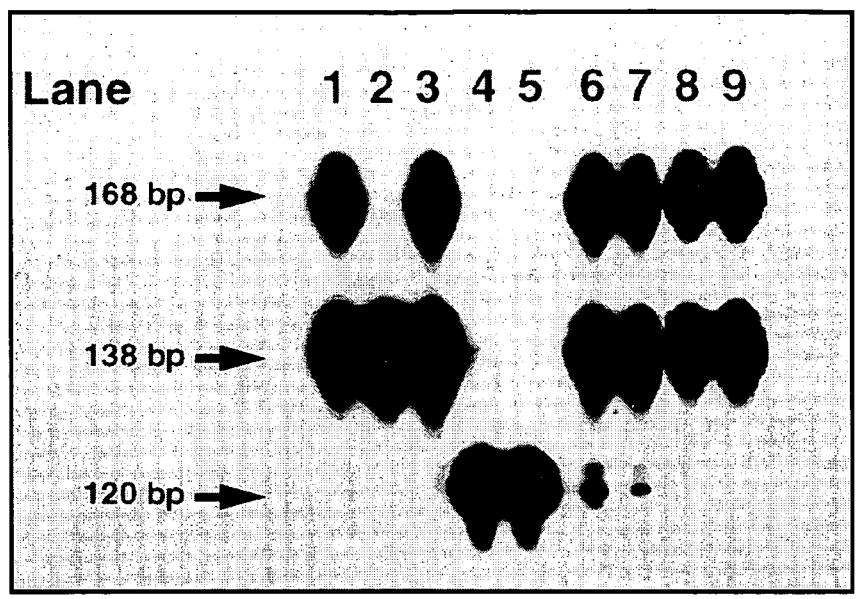
FIG. 4 is an autoradiogram (6 days exposure at −70° C.) of SW16 microsatellite alleles confirming chimerism in a pig C019.

At the cellular level the presence of a Meishan-specific SW16 microsatellite allele (120 bp) was used to detect chimerism (FIG. 4). The presence of the Meishan and Duroc SW16 alleles in DNA samples from various tissues of the chimeric pig designated C019 was confirmed by an autoradiogram (6 days exposure at −70° C.) of SW16 microsatellite alleles. Lane 1 contained a Duroc control DNA sample. Lane 2 contained a sample from the dam and lane 3 from the sire of the Duroc blastocysts injected with the Meishan ES cells. Lanes 4 and 5 contained samples from the dam and the sire, respectively, of the Meishan ES cell line 1192M. The dam and the sire of the ES cells both carried the Meishan specific 120 bp allele. Lanes 6–9 showed alleles present in various tissue samples (lane 6, blood sample 1; lane 7, blood sample 2; lane 8, skin sample 1; and lane 9, skin sample 2) examined from chimeric pig C019. Analysis of DNA samples indicated that cells derived from the Duroc recipient blastocyst in this individual were heterozygous for the Duroc alleles 138 and 168. However, DNA samples also contained DNA from the Meishan ES cells which carried the 120 bp allele. The presence of the 120 bp allele confirmed chimerism in this individual. Duroc alleles inherited from the sire and dam are the 138 and 168 bp bands (lanes 2 and 3) while both the sire and dam of the porcine ES cell line are homozygous for a 120 bp allele (lanes 4 and 5).

Various tissues from pig C019 were tested for the presence of the 120 bp allele. Tissues which were shown to be positive include ear, skin from the black spots and the blood. Lanes 6 and 7 show the presence of the Meishan allele as well as the Duroc alleles in 2 different blood samples indicating the presence of both cell types (Duroc cells from the recipient blastocyst and Meishan cells from the ES cell line) in the chimeric offspring. Variation in the quantity of 120 bp fragment amplified between tissues was evident.

Although accurate measurement of the percentage of chimerism is not available from this data, it appeared that the blood samples are consistently higher in Meishan DNA than the other tissues sampled.

Figure 5:
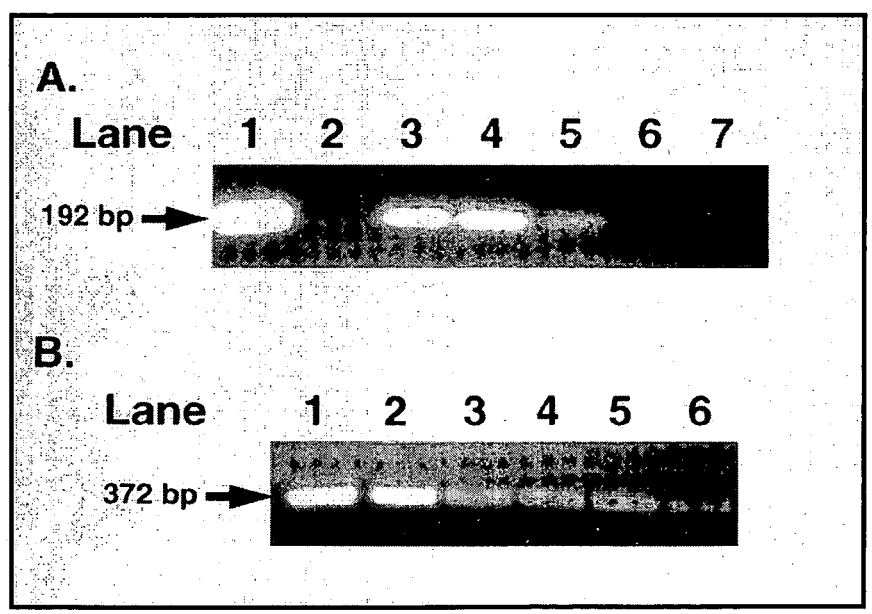
FIG. 5 shows a photograph 1% agarose gels stained with ethidium bromide revealing PCR products.

Further, because one of the ES cell lines (M1192) had a male chromosomal complement (XY), analysis of a Y-specific chromosome sequence was used to confirm the presence of Meishan cells in the resultant female offspring. These results paralleled the data obtained with the SW16 marker. FIG. 5 is a photograph of ethidium bromide stained 1% agarose gels of PCR products showed: Panel A: Gel showing the 192 bp Y-specific PCR product for control and chimeric animals. Lane 1 contains a sample from a control male pig. Lane 2 contains a sample from a control female pig. Lane 3 contains a skin sample from the female chimeric pig (C019). Lane 4 contains a blood sample from pig C019. Lane 5 contains a sample of ear, tail and skin (ETS) from C019. Lane 6 contains a nose sample from C019. Lane 7 contains a tail sample from C019. Panel B: Control gel showing a 372 bp PCR fragment of the porcine α-lactalbumin gene. The gel contains all the samples used in the Y-specific probe analysis except for the control male pig sample. Lane 1 contains a sample from the control female pig. Lane 2 contains a sample from the C019 skin. Lane 3 contains a C019 blood sample. Lane 4 contains a C019 ETS sample. Lane 5 contains a nose sample of C019. Lane 6 contains a tail sample from C019. As with the SW16 marker, the level of Y-specific PCR product varied among the tissues analyzed, with the largest amount of product occurring in the blood samples. The control gel confirmed the presence of intact DNA in each sample.

6. Uses for Embryonic Stem Cells a) Xenografts (xenotransplantation) Cells, tissues or organs with exogenous major histocompatibility or other foreign or endogenous antigens and/or genes that will decrease rejection by the host organism of these transplanted materials may be produced by means of the present invention. Exogenous foreign or homologous DNA is transferred to ungulate ES-cells by electroporation, exposure to calcium phosphate, microinjection, lipofection, retro- or other viral or microbial vector, or other means. The ES-cells are screened for incorporation for this DNA or expression of antigens, directly transferred to embryos to produce chimeras, or used in nuclear transfer systems to clone ungulates. These cells, tissues and organs are harvested from embryos, fetal, neo-natal or resulting adults for xenotransplantation. In this manner, humanized-ungulate transplants e.g. kidney for kidney, are contemplated.

Production of differentiated cells for replacement, repair or augmentation of damaged, non-functional, or impaired cells or tissues are another use. Exogenous foreign or homologous DNA are transferred to ungulate ES-cells by electroporation, calcium phosphate, microinjection, lipofection, retro- or other viral or microbial vector or other means. The ES-cells are screened for incorporation for this DNA, directly transferred to embryos to produce chimeras, or used in nuclear transfer systems to clone ungulates. These cells and tissues are harvested from embryos, or resulting adults for use to repair or augment some defect. For example, organs from ungulate fetuses, and neonates, may be used in treating Parkinson's patients, persons who had heart attacks, or spinal cord injuries.

b. Production of specific proteins or other biological molecules Pharmaceuticals, diagnostics, or antibodies, used in manufacturing or processing, as food supplements, additives and the like, are produced using porcine, bovine, ovine and caprine ES-cells. Exogenous foreign or homologous DNA are transferred to ungulate ES-cells by electroporation, calcium phosphate, microinjection, lipofection, retro- or other viral or microbial vector or other means. The ES-cells are screened for incorporation for this DNA, or are directly transferred to embryos to produce chimeras, or are used in nuclear transfer systems to clone ungulates. These proteins or other molecules are harvested from ungulate embryos, fetuses, neonates or resulting adults for further purification. For example, human blood clotting factor IX may be produced in pig, cattle, sheep, and goat milk for treatment of hemophilia.

Transgenic swine, bovine, ovine and caprine may be produced with altered tissue or milk proteins which may be collected for commercial or experimental use. (Table 6).

Examples of the following pharmaceutical, therapeutic, processing, manufacturing or compositional proteins that may be produced in this manner include: blood proteins (clotting factors VIII and IX, complement factors or components, hemaglobins or other blood proteins and the like), hormones (insulin, growth hormone, thyroid hormone, gonadotrophins, PMSG, trophic hormones, prolactin, oxytocin, dopamine, catecholamines and the like), growth factors (EGF, PDGF, NGF, IGF's and the like), cytokines (interleukins, CSF, GMCSF, TNF, TGFα and β and the like), enzymes (tissue plasminogen activator, streptokinase, cholesterol biosynthetic or degradative, digestive, steroidogenic, kinases, phosphodisterases, methylases, de-methylases, dehydrogenases, cellulases, proteases, glycosolases, lipases, phospholipases, aromatase, cytochromes adenylate or guanylate cyclases and the like), hormone or other receptors (LDL, HDL, steroid, protein, peptide, lipid or prostaglandin and the like), binding proteins (steroid binding proteins, growth hormone or growth factor binding proteins and the like), immune system proteins (antibodies, SLA or MHC genes, antigens (bacterial, parasitic, viral, allergens and the like), translation or transcription factors, onco-proteins or protoonco-proteins, milk proteins (caseins, lactalbumins, whey and the like), muscle proteins (myosin, tropomyosin and the like).

In a typical situation, the nucleotide sequence encodes a precursor form of the protein ultimately harvested from the transgenic pigs, cattle, sheep and goats. Of course, certain products are not recoverable for production from certain tissues. The method disclosed herein for determining what cell types express a certain construct will be useful in determining what tissue is suitable.

TABLE 6

EXAMPLES OF PROTEINS THAT ARE RECOVERABLE FROM TRANSGENIC PIG, CATTLE, SHEEP AND GOAT BODY FLUIDS

| Body Fluids | Protein |
| --- | --- |
| Milk[a] (almost all proteins) | Factor IX |
| | Lactoferrin |
| | Lactalbumin |
| | EGF |
| | IGF |
| | FGF |
| | NGF |
| Urine (small proteins on the order of 10–100 aa) | (Gonadotrophins) |
| | FSH |
| | LH |
| | Oxytocin |
| | PRL |
| Blood | Clotting factors |
| | Hemoglobin |
| | Plasmin |
| | TPA |
| Saliva | EGF |
| | Growth factors |
| | Digestive enzymes |

[a]If using pig, cattle, sheep, and goat milk as a protein source, a mammary specific promoter is needed for the transgene, for example, the α-lactalbumin promoter.

In an illustrative embodiment, the production of human clotting factor IX (FIX) in the milk of transgenic swine, cattle, sheep and goats via embryonic stem cells is accomplished by the following protocol. The human clotting factor IX protein encoding sequence is excised from the FIX cDNA (Clark et al., 1989) and ligated to a mammary specific promoter (such as the alpha lactalbumin promoter) to produce the transgene construct. This construct is electroporated into the stem cells. A gene for a selectable marker such as neo is co-electroporated so that following a recovery period, the transgenic cells will be selected by adding G418 to the media which will kill all cells that have not incorporated and are not expressing the neo gene. These stem cells are injected into porcine, bovine, ovine and caprine embryos to form chimeras or are used for cloning to directly produce transgenic animals. The animals are screened using the transgene as a probe and mRNA from mammary tissue biopsy is tested for appropriate expression of the FIX gene. The transgenic females are bred and milked and the FIX extracted from the milk.

c. Enhance genetic traits in livestock—Porcine, bovine, ovine and caprine ES-cells are used to improve disease resistance; growth rate and efficiency; milk production, quality and composition; carcass quality and composition; body composition; reproductive efficiency and performance. Further, improved performance by controlling expression of a specific gene during development and growth to adulthood, including auto-immunization against pathogens, increased secretion of growth promotants, stimulation of reproductive processes including lactation is contemplated. Genetically-engineered individuals resulting from ungulate ES-cells serve as founder animals for new breeds or strains of swine, cattle, sheep and goats. For example, altered milk protein composition allows for increased survivability of offspring and increased growth.

Removing or altering deleterious alleles, genes, or DNA sequences is effected using homologous recombination. Specific DNA sequences are removed, introduced or altered to manipulate the biology of the individual. Genetically-engineered individuals resulting from porcine, bovine, ovine and caprine ES-cells serve as foundation animals for new breeds or strains of swine, cattle, sheep and goats. For example, removing the gene encoding the enzyme responsible for producing the hormone that causes boar taint will yield an animal not showing that condition.

d. Production of genetically engineered identical offspring from other species is accomplished by the transfer of ES-cell nuclei to embryonic cells or unfertilized oocytes, such that resultant cell lines, tissues, organs or offspring contain all or part of the genetic material of the transferred nucleus or nuclei. These individuals are useful for increasing product uniformity; gene mapping, histocompatibility; propagating specific desirable or genetically (DNA-transformed) genotypes, providing large numbers of genetically identical cells, tissues, organs and animals for transplantation and research purposes.

ES-cells from specific cell lines, either with or without an exogenous gene or genes, are transferred by micromanipulation to foreign cytoplasm such as enucleated oocytes or embryonic cells. The resultant cells are cultured to establish new lines, used to form chimeric embryos, tissues, and/or organs or transferred to surrogate mothers for production of genetically engineered offspring. Transfer of multiple cells or a single ES-cell or nucleus to an enucleated oocyte or embryonic cell is accomplished through micromanipulation. Fusion of the transferred cell or nucleus is accomplished with electropulses, exposure to a fusion agent such as Sendai virus or polyethylene glycol, or by exposure to ionophores that alter the ionic fluxes of the cell membranes. Genetically-engineered individuals resulting from ungulate ES-cells serve as foundation animals for new breeds or strains of ungulates. For example; ES-cells carrying a transgene may be fused to enucleated oocytes to produce cells with identical nuclear DNA for production of cloned cells, tissues, organs (kidneys transplant) or animals.

7. Gene Transfer

Cell lines which have produced tumors in SCID mice are preferred as vectors to carry transgenes into chimeric animals by methods of the present invention. The cell with the transgene may be carried by a variety of methods into the cell. These methods include electroporation, microinjection, lipofection, retroviral infection and calcium phosphate. The cells are screened with the antibiotic G418 (when constructs contain the neo gene) or other appropriate screening drug or compound. The remaining colonies after screening are cloned and checked for incorporation of the transgene via methods known to those of skill in the art, including PCR, Southern, Northern or Western analysis.

8. Efficiency of Stem Cell Production in Swine

Embryos from Duroc, Meishan, Yorkshire and [Landrace X Yorkshire (L X Y)] lines of swine were collected for development of swine embryonic stem cell lines. Day 8 hatched blastocysts were surgically flushed from donor animals and cultured in 24 well plastic culture plates in the presence of embryonic stem cell development medium. Embryos were examined on day 3, 7 and 14 after the initiation of culture, the attachment of the blastocyst and amount of cellular growth were recorded. The type of cellular attachment and growth was classified as either trophoblastic or inner cell mass-like. A total of 391 blastocysts were collected and cultured (110 Duroc, 84 Yorkshire, 44 L X Y and 153 Meishan). Duroc blastocysts tended to attach faster and showed more inner cell mass-like attachment than did either the Yorkshire or the L X Y crosses. The frequency of inner cell mass-like attachment differed among breeds. The percentage of embryos that exhibited this attachment was 16.4%, 11.1%, 5.9% and 4.5% for the Duroc, Meishan, Yorkshire and L X Y, respectively. The frequency of Duroc inner cell mass-like attachment was higher ($P<0.05$) than either the Yorkshire or the L X Y, but was not different from Meishan embryo attachment frequency. There was also an effect of individual donor on occurrence of inner cell mass-like attachment ($P<0.05$). Embryos from individual donors ranged from 0 to 50% in their inner cell mass-like attachment frequency. However, the donor effect was not dependent on breed. The results indicate that ability of porcine embryos to attach and thus potentially grow in culture is effected by breed and donor of the embryos. For additional information on efficiency see Tables 7 and 8.

TABLE 7

| Breed of Donor | # Embryos Collected | # Embryos Sub-Cultured | % Sub-Cultured |
|---|---|---|---|
| Meishan | 337 | 53 | 15 |
| Yorkshire | 84 | 19 | 23 |
| Duroc | 243 | 49 | 20 |
| Duroc X York | 126 | 14 | 11 |
| Totals | 790 | 135 | 17 |

TABLE 8

| Breed | # of Donors | # of Embryos | # Embryos/Donor |
|---|---|---|---|
| Meishan | 14 | 203 | 14.5 |
| Duroc | 29 | 228 | 7.9 |
| Yorkshire | 21 | 167 | 7.9 |
| TOTALS | 45 | 598 | 13.2 |

9. Antibiotic Resistance

Antibiotic G418 (Geneticin) is an aminoglycoside related to Gentamicin frequently used as a selection agent for mammalian cells which have incorporated and are expressing the neo gene. Non-expressing cells die after a few days exposure to the drug. The dose used for selection of mouse cells commonly ranges from 125 to 400 mg/ml of media.

In order to determine the optimal dose of G418 for selection of porcine neo expressing cells, a dose curve was performed. Both mouse ES-D3 cells and porcine D195 cells were plated into 12 well plates with $1\times10^4$ cells per well in 2 ml of conditioned stem cell media. The day following plating, G418 containing media was added at the following concentrations: 0, 250, 500, 750, 1000 or 1250 µg/ml. Cells were dispersed and counted on days 2, 4, 6 and 8. The number of live cells in each treatment well as determined by trypan blue exclusion, was divided by the number of cells in the untreated control well for each cell type each day. After 48 h, 68, 6, 2, 2 and 0% of the mouse cells were alive at the respective doses while 70, 54, 75, 29 and 5% of the porcine cells survived. By day 8, only 0.2 ±0.3% of ES-D3 cells were alive in the 250 µg dose and 0% in all higher doses. At this time 92.7±4.7% of D195 cells were alive in the 250 µg treatment group. However, at the 750 µg dose only 0.03%±0.03% were alive. Therefore, it was determined that the best dose to select D195 cells is 750 µg/ml.

In order to determine if other porcine ES-like cells will also require higher doses of G418, this experiment was repeated with mouse ES-D3, D195 and 2 other porcine lines designated M2–176, M2–158. The latter two lines show ES morphology. These were treated with 250, 750 and 1250 µg/ml G418 for 8 days, then cell counts were determined as in experiment 1. As in the previous experiment, the percent of live cells was different between the mouse ES-D3 and D195 lines at the 250 µg dose ($P<0.01$) and was similar at both higher doses. However, D195 cells were more resistant to G418 than any other porcine lines ($P<0.05$) at 250 µg/ml. These results are interpreted to mean that mouse ES-cells are more sensitive to G418 than D195 cells. However, these cells also respond differently than other porcine lines indicating that the G418 selection dose must be optimized for each cell line.

10. Factors in Mouse Tumor Production by ES-cells

Murine embryonic stem (ES-D3) cells, e.g, line ES-D3, produce teratomas when introduced into syngeneic or immune compromised mice. However, factors involved in tumor development have never been identified. In order to test the hypothesis that injection site, cell number injected and sex of the recipient mouse alter tumor formation, mouse ES-D3 cells were injected into severe combined immunodeficient (SCID) mice and allowed to grow for 17 to 21 days. At necropsy, tumors were harvested, evidence of metastasis was noted, and tissue was fixed for histological examination. In experiment 1, $2\times10^6$ cells were injected into the testes and kidney of subcutaneous of male SCID mice. Tumor incidence was 100% for testes (9/9) and kidney (10/10) but only 83% (5/6) for subcutaneous injections.

In experiment 2 the effect of number of cells injected on tumor incidence was assessed. Injections of $2\times10^6$, $2\times10^4$, $2\times10^2$ or 0 were each made in the testes of 4 mice. After 17 cells only the $2\times10^6$ group (4/4) had grossly visible tumors. One mouse in the $2\times10^4$ group (1/4) had a teratoma identified histologically. In the $2\times10^6$ group the total tumor weight ranged from 0.73 g to 2.66 g. Abdominal metastases to the mesentery were present in all mice. Nervous and glandularlike tissues were consistently identified in the teratomas with variable amounts of keratinized skin, ciliated epithelial cells, goblet cells, and cartilage.

Because the ES-D3 cells are derived from female embryos, experiment 3 compared the ability of tumors to form in male and female mice injected with $2\times10^6$ ES-D3 cells into the kidney. Teratomas occurred in both male (6/6) and female (6/6). Metastases were found in 66% of the female and only 33% of the males in this experiment. Mean tumor weight was not different (1.1+0.39 g vs. 1.6+0.68 g) between the sexes. These data are interpreted to show that 1) Injection site is not critical for tumor formation, however sites are less advantageous. 2) Greater than $2\times10^4$ cells are necessary for tumor formation. 3) Female ES-cells produce tumors in both male and female recipients. These experiments are models for experiments in ungulates to answer similar questions.

11. ES-cell Lines

A cell line designated D195 was produced by culturing swine embryo cells on plastic in BRL-conditioned stem cell medium. Characteristics of this line included the following:
1) positive for swine specific alleles (e.g. alpha-lactalbumin) as determined by PCR;
2) grows in distinct colonies on both plastic and STO feeder cells;
3) produces embryoid bodies if allowed to grow to confluence in the culture vessel (embryoid bodies do not produce tumors, indicating that they are differentiated;
   embryoid bodies do not produce pregnancies when transferred back to recipient pigs;
   however they produce rather extensive trophoblastic vesicles)
4) culture doubling time is approximately 18–24 hours;
5) cells are consistent with pluripotent cells because they differentiate into neuronal-like morphologies when incubated with retinoic acid and muscle-like morphologies when incubated with dimethylsulfoxide (DMSO);
6) cells are 8–15μ diameter, have a 5% cytoplasmic to 85% nuclear ratio, and are round when isolated.

Procedures for Processing D195 are: Thawing:

Thaw at 36° C. for about 1 min. Re-suspend in 9 ml of stem cell medium (SCM), centrifuge at 300 g for 5 min to pellet cells, remove supernatant. Re-suspend cells to $1\times10^6$ cells/ml in conditioned stem cell medium (CSCM).

Subculture:

Add 2 mls of cell suspension to 18 ml of CSCM in 75 cm$^2$ tissue culture flask. Cells should be sub-cultured every 2–3 days. Plate at a density of $2\times10^6$ cells/75 cm$^2$ tissue culture flask. Cells should be sub-cultured when they are about 80% confluent.

To subculture, pour off medium and wash cells with 10 ml of calcium and magnesium free phosphate buffered saline (PBS). Add 2 ml of trypsin-EDTA, incubate at 37° C. for 1–2 min. Dislodge cells by gentle agitation of flask and rapping against the palm of the hand. Add 4 ml of CSCM, wash sides of flask with CSCM and place all contents in a 50 ml conical centrifuge tube. Disaggregate cells by gentle pipetting of the medium several times. Count cells and re-suspend to $1\times10^6$ cells/ml. Add 2 mls of cell suspension to 18 ml of CSCM in 75 cm$^2$ tissue culture flask. Cells will generally need sub-culturing every 2–3 days.

Cryopreservation:

The D195 cells are frozen at $2-4\times10^6$/ml. Add 0.5 ml of freezing medium to a cryovial, then add 0.5 ml of cell suspension in CSCM ($2-4\times10^6$ cells/0.5 ml), mix gently, and immediately place into a styrofoam box and place in the −70° C. freezer. Freeze over night. When frozen place into liquid nitrogen at −196° C.

Materials and Methods:

Collection of Swine, Bovine, Ovine and Caprine Embryos and Isolation of ES-like Cells.

1. Control of Ovulation and Hatched Embryo

Collection: Females are checked for estrus twice daily, and are inseminated at estrus to be donors. Embryos are collected on the following days depending on the species: pig 5.5–8.0 as expanded or hatched blastocysts; cow 5.5–10 days, early to hatched blastocysts; sheep 5–9 days, early to hatched blastocysts; goat 5–9 days, early to hatched blastocysts.

For embryo collection hatched blastocysts were flushed from the uterus of the donors 6–8 days after the first day of estrus (d=0) with Dulbecco's phosphate buffered saline (D-PBS) which contained 5% fetal calf serum (FCS, Sigma #F-2442, Sigma Chemical Co., St. Louis, Mo.) or Beltsville Embryo Culture Medium [BECM] which contained 1% bovine serum albumin (BSA, Sigma # A-9419, Sigma Chemical Co., St. Louis, Mo.). BCEM is a modification of TLHGL swine embryo culture medium (Hagen et al., 1991) supplied by Vernon G. Pursel (USDA-ARS), Beltsville, Md., personal communication. The modified BECM formula includes; NaCl (90 mM), KCl (4.83 mM), NaHCO$_3$ (2.14 mM), Hepes (10.91 mM, free-acid), MgCl$_2$.6H$_2$O (0.54 mM), L-glutamine (1.0 mM), calcium lactate (2.14 mM), glucose (0.55 mM), mannitol (11.0 mM), sodium lactate (19.3 mM), sodium pyruvate (0.27 mM), taurine (7.0 mM), EDTA (0.08 mM), phenol red (0.01 g/l) and gentamycin sulfate (0.05 g/l). In the modified formula there was a NaH$_2$PO$_4$.H$_2$O and CaCl$_2$. Hatched blastocysts are cultured in 96-well microtiter plates Nunclon™, NUNC Corp.).

Embryos were washed three times in either D-PBS or BECM and cultured individually on mitomycin C-inactivated mouse embryonic fibroblast (STO) monolayers with 2 ml of conditioned stem cell medium (CSCM). Conditioned stem cell medium is comprised of 40% Dulbecco's Modified Eagle's Medium DMEM (Sigma Hybrimax brand, catalogue No. D6655), containing L-glutamine, 4500 mg glucose/L; Sigma Chemical Co., St. Louis, Mo. with the following supplements: 20% FCS, 0.1 mM 2-mercaptoethanol, 50 IU penicillin/L, 50 μg streptomycin/L, 10 mM/L MEM non-essential amino acids (Sigma #M7145, Sigma Chemical Co., St. Louis, Mo.), nucleosides (0.03 mM adenosine, 0.03MM guanosine, 0.03 mM cytidine, 0.03 mM uridine, and 0.01 mM thymidine)[43] and 60% Buffalo Rat Liver cell conditioned medium (BRL-CM containing a total of 20% FCS, and the outlined supplements mentioned herein (Smith and Hooper, 1987; Hooper, 1987)).

After 7–9 days in culture, the whole embryonic cell colony was partially disaggregated with buffered trypsin/EDTA solution (0.25% trypsin, 0.4% EDTA in Ca++-free, and Mg++-free phosphate buffered saline; 1.0% NaCl, 0.025% KCl, 0.025% KH$_2$PO$_4$ and 0.114% Na$_2$HPO$_4$, pH7.2) for 1 min at 37–39° C. The trypsin/EDTA solution was diluted 1:1 with CSCM, triturated, and the partially disaggregated cells were re-seeded onto new mitomycin C-inactivated STO feeder layers or primary embryonic fibroblasts. For all subsequent passages the cells were plated onto fresh feeder layers with BRL conditioned stem cell media (CSCM). Cells were subcultured as necessary onto increasingly larger culture dishes.

For chimera production, embryos were collected from Duroc donor gilts 6–7 days after the onset of estrus. Morula, blastocyst and expanded blastocyst stage embryos were washed through three changes of medium and placed in 100 µl drops of D-PBS with 5% FCS overlaid with paraffin oil (Saybolt viscosity, 125/135, Fisher Scientific, Springfield, N.J.) in a humidified air environment at 39° C. until micromanipulation was performed (up to 2 hr). The embryos were grasped by a fine glass holding pipette attached to a micromanipulator (Narashige Inc., Tokyo, Japan). Approximately 5 to 10 ES cells (range 1–20 cells) were placed into the cell mass (morula) or into the blastocoel cavity (blastocyst and expanded blastocyst) by means of a glass injection needle, 25–30µ in diameter, which was attached to a micromanipulator. After injection, the embryos were immediately transferred to recipient gilts which exhibited the onset of estrus 24 h after the embryo donor.

2. Subculture of STO Cells: When plates of STO cells become or approach confluence (80%), they are subcultured. Medium is removed from the plates, and 2 ml of freshly thawed (thaw in 37° C. $H_2O$ bath) trypsin EDTA (0.25%; 0.04%) added. Plates are placed in a 38° C. incubator for 5 minutes. Trypsin is neutralized by adding 2 ml of serum-DMEM (sDMEM, complete medium; warmed in the 37° C. $H_2O$ bath) to each plate. Cells are then vigorously pipetted to form a single cell suspension. Fresh medium is added to effect a 1:2–1:10 dilution. The dilution ratio is adjusted to the degree of confluence and number of the plates of cells. Plates are gently swirled to ensure uniform plating. Plates are then placed in a 38° C., 5% $CO_2$ incubator. Medium is changed every 2 days with cells growing to confluence (80%) within 2–5 days, depending upon seeding density.

3. Preparation of Feeder Layers: STO cells are treated two days prior to use as feeder layers. Using plates of STO cells that are nearly confluent (generally one day prior to being confluent), medium is aspirated, and carefully replaced with 2–4 mls of a 10 ug/ml solution of Mitomycin C (Sigma Chemical Co.) and returned to 38° C. incubator for 2–3 h. At this time, mitomycin C solution is removed by washing each plate 2–3× with 5 ml of sterile PBS, pH 7.2. Medium is replaced with 10 ml of sDMEM and plates are returned to the incubator at 38° C. for 24 h. After 24 h the medium is replaced with fresh medium and again when used as a feeder layer. Feeder layers can be kept up to ten days before use.

4. Embryo Culture (Unhatched Embryos): Embryos are washed 3 times in modified Whitten's or other embryo culture medium and placed individually into culture vessels containing 1) a reformed feeder layer of fibroblasts (STO cells) or 2) no feeder layer; with either stem cell Modified Whitten's medium (SCW-2) (Table 18) with 20% fetal calf serum, penicillin-streptomycin, $10^{-4}M$ 2-mercapoethanol, and non-essential amino acids (for feeder layers), or stem cell medium (SCM) for a feeder layer, or CSCM (with or without feeder layers).

ES-cell culture medium (SCM) consists of Dulbecco's modified Eagle's medium (DMEM; containing L-glutamine, 4500 mg glucose/L) with 0.1 mM 2β-mercaptoethanol, 50 IU penicillin/L, 50 µg streptomycin/L, 10 mM/L MEM non-essential amino acids (Robertson, 1987) and 20% FBS.

After the embryos are collected, they are washed 3 times with fresh culture medium to dilute contaminants from the tract. Embryos are transferred to micro drops of W-2 media under oil and culture to hatching. This will only occur if 6-day embryos or younger are flushed out. When hatched blastocysts are obtained, they are transferred to an individual well in a 24 well plate. Each well should contain 1 ml media (Stem Cell Media, SCM) if using STO feeder layers, and Conditioned Stem Cell Media (CSCM) if not using a feeder layer. Initial stages of culture are carried out. After 24–48 h of culture the embryos hatch from the zone pellucida and attach to the culture dish.

5. Stem Cell Isolation and Culture: Embryonic stem cells are isolated from the attached embryos and maintained in culture by the following protocol. The inner cell mass (ICM) enlarges during the first few days of culture. After enlargement, the ICM is dislodged from the underlying cells and washed through two changes of calcium/magnesium-free PBS. The ICM is then transferred to a 50 µl drop of trypsin solution (0.25% trypsin, 0.4% EDTA in $Ca^{++}$, $Mg^{++}$-free phosphate buffered saline, PBS see Table 13; 1.0% NaCl, 0.025% KCl, 0.025% $KH_2PO_4$) and incubated for 1–5 minutes at 38° C.

The cells are disaggregated with a fine Pasteur pipette. The contents are then transferred to a fresh drop of CSCM with 20% FCS in a fresh culture vessel with or without a feeder layer. The cultures are inspected daily for the appearance of nests of round stem cells which appear after 7–8 days (range 2–21 days) culture. Colonies are dissociated from the feeder layers, as described above, treated with trypsin and passed to fresh feeder layers. In successful cultures, small nests or clusters of stem cells appear after 2–3 days of subculture. These nests are isolated, dispersed and plated on fresh culture vessels with or without feeder layers. The cells at this stage require subculture every 3–10 days depending on the growth rate. Cells have spent media replaced with fresh media every 2–3 days. To preliminarily characterize the pluripotent nature of ES-cell lines microscopic observation of undifferentiated morphology is used. ES-cells are typically small and rounded, possessing large dark nuclei which contain one or more prominent nucleoli.

ES-cells are purified, as described herein, from feeder cells or from differentiated porcine cells (lines may be developed entirely in conditioned medium (CSCM) alone). Further characterization requires indirect immunofluorescent staining of ES-cells for lack of the cytoskeletal structural proteins, cytokeratin 18 and vimentin, which are only expressed in differentiated cell types. In vitro differentiation of pluripotent ES-cells into endoderm, ectoderm or mesoderm with concomitant loss of typical undifferentiated ES-cell morphology and positive staining with anti-cytokeratin 18 and anti-vimentin antibodies may be induced.

6. Culture of Embryonic Stem Cells: After established, stem cell cultures grow rapidly, dividing every 18–36 hours. The cells should be kept at relatively high densities to ensure that a high rate of cell division is maintained as this minimizes the level of spontaneous differentiation. The cultures are re-fed daily, or according to the acidity of the medium, and subcultured at 3–4 day intervals. Cells are routinely grown in the same medium (CSCM) as for the original embryos from which they were derived.

The stem cells are subcultured (passaged) when the plates approached confluence. The cells are re-fed 2–3 hours prior to passage to improve the cell viability. The medium is aspirated and the cell surface washed with 5 ml of sterile PBS. The PBS is replaced with 0.5–3 ml of trypsin EDTA and incubated at 38° C. for 1–5 minutes. The plate is then removed from the incubator and the suspension is pipetted vigorously using a sterile plugged Pasteur pipette. After pipetting the cell suspension is checked visually under low-power (40×) of a light microscope to ensure that it is relatively free of cellular aggregates. The cells are pelleted in a centrifuge tube at 1000×g for 5 minutes the supernatant aspirated and the cells re-suspended in 10 ml of medium (CSCM). Finally, the cell density is determined and the cell suspension re-plated onto feeder plates (1–2×10⁶ cells per 100 mm plate) containing 10–12 ml of complete medium.

Use of ES-Cells to Form Chimeras

7. Production of Chimeras: Five to 20 (range one to 30) ES-cells, generally from a culture passage of between 10–20, are placed into the cell mass (morula) or into the blastocoele cavity (blastocyst and expanded blastocyst) by means of a glass injection needle, 25–30μ in diameter, which is attached to a micromanipulator. After injection, the embryos are immediately transferred to recipient gilts, cows, ewes, or does which have estrus 24 h after the embryo donor.

Chimeras are preferably entered designed so that they are easily screened, e.g. using coat color markers (i.e., Meishan X Duroc, Angus X Hereford for cattle, Dorset X Lincoln (homozygous black strain) for sheep, Saanen X Toggenburg or Black or Brown Nubian for goats). Resultant individual chimeras will have patches of different color skin and hair derived from each of the embryonic cell lineages.

8. Production of Chimeras and Clones Via Nuclear Transfer: Chimeras are produced by aggregation of ES-cells with pre-implantation embryos of the following stages: one-cell, two-cell, four-cell, eight-cell, 16-cell, 32-cell, morula, blastocyst, and hatched blastocyst.

Nuclear transfer offspring or clones are produced by fusion or injection of ES-cell nuclei with enucleated, pre-implantation embryonic cells of the following stages of embryo: oocytes, one-cell, two-cell, four-cell, eight-cell, 16-cell, 32-cell, morula, blastocyst, and hatched blastocyst.

In vivo differentiation of pluripotent ES-cells is confirmed by their ability to participate in the formation of chimeric offspring. Morula, blastocyst and expanded blastocyst stage embryos are placed in 100 μl of PBS under oil. The embryos are grasped by a fine glass holding pipette attached to a micromanipulator (Narashige Inc., Tokyo, Japan).

9. Breeds of Swine: The Meishan breed is from the lake Taihu region near Shanghai. Taihu pigs appear to be the most prolific in China. The region is characterized as temperate, with temperature averaging 15.7° C. and ranging from an annual low of −9.0° C. to an annual high of 38.2° C. The Chinese Taihu breeds of pig are highly prolific and attain puberty at an early age, but have poor growth rates and carcass quality. Chinese Meishan pigs range from light grey to dark black in color with varying degrees of white spots. Meishan pigs characteristically have white feet and hooves, extremely wrinkled faces and large, pendulous ears. Domestication of the pig in China dates back to a least 3,000 B.C. and, over time, Chinese pigs have contributed to the development of world pig breeds. A large number of pigs from South China were imported into the Roman Empire in the 3rd century B.C. and used to improve European breeds. From the 16th through the 18th century A.D., pigs from South China were imported to England and used in the development of modern breeds, particularly the Yorkshire and Berkshire. By the end of the 18th century, breeds with Chinese ancestry had replaced almost all indigenous English breeds.

The Berkshire and Yorkshire breeds in the United States originated with importations from England in 1823 and 1893, respectively. Chinese pigs, introduced into 19th century America, also played a role in the formation of the Poland China and Chester White breeds. Importation of promising foreign breeds has a long tradition in livestock production, with Landrace (first imported from Denmark in 1934) the most recently introduced pig breed that has contributed substantially to U.S. pork production.

The Duroc breed is a totally American breed and dates back to the 1870's when a combination of the Jersey Red from New Jersey and the Duroc from New York formed a breed known as Duroc-Jersey, later to become know as simply the Duroc. The Duroc is a very durable breed and has been shown to have high growth rate and good marbling characteristics. These two characteristics, fast growth and carcass quality, plus a strong confirmation has helped to place the Duroc at the top (along with Yorkshire) of purebred registrations in the U.S. Durocs are solid red in color, varying from light to dark, and have medium-sized, pendulous ears.

10. Media: SCM Stem cell medium (SCM) consists of Dulbecco's Modified Eagle's Medium (DMEM; containing L-glutamine, 4500 mg glucose/L; Sigma Hybrimax #D6655, Sigma Chemical Co., St. Louis, Mo.) and the following supplements: 20% FCS, 0.1 mM 2-mercaptoethanol, 50 IU penicillin/L 50 μg streptomycin, L, 10 mM/L MEM non-essential amino acids (Sigma #M7145, Sigma Chemical Co., St. Louis, Mo.), nucleosides (0.03 mM adenosine, 0.03 mM guanosine, 0.03 mM cytidine, 0.03 mM uridine, and 0.01 mM thymidine) (Robertson, 1987).

CSCM Conditioned stem cell medium (CSM) is consists of 40% Dulbecco's Modified Eagle's Medium (DMEM) and 60% Buffalo Rat Liver cell (BRL-3A, ATCC CRL#1442) conditioned medium (BRL-CM) (Smith and Hooper, 1987; Hooper, 1987) containing a total of 20% FCS, and the following supplements: 0.1 mM 2-mercaptoethanol, 50 IU penicillin L, 50 mg streptomycin L, 10 mM L MEM non-essential amino acids, nucleosides (0.3 mM adenosine, 0.03 mM guanosine, 0.03 mM cytidine, 0.03 mM uridine, and 0.01 mM thymidine). Other media and solution formulations are shown in Tables 9–18.

TABLE 9

MEDIA

| MEDIA LABEL | DESCRIPTION | CELL TYPE |
|---|---|---|
| DMEM | Basal medium for all cell culture | — |
| sDMEM | DMEM + FBS + PEN/STREPT | BRL + STO |
| BRL-CM | sDMEM harvested from BRL cells used to make CSCM | — |
| SCM | [DMEM + FBS] + each additive* | embryonic stem cells on feeder layers |
| CSCM | [BRl-CM] + FBS + each additive*] + SCM | embryonic stem cells no feeder |

*Additive = β-mercaptoethanol, antibiotics stock, nucleosides stock, and MEM non-essential amino acids
PEN = penicillin
STREPT = streptomycin

TABLE 10

DULBECCO'S MODIFIED EAGLE'S MEDIUM (DMEM) FOR THE CULTURE OF ANIMAL CELLS IN AN *IN VITRO* ENVIRONMENT

| Ingredient | mM | gm/L |
|---|---|---|
| Dulbecco's modified Eagle's medium (DMEM) (Sigma-Hybrimax D 6655) containing: | — | 13.4 |
| NaCL | 110.0 | 6.4 |
| Na₂HPO₄ | 0.80 | 0.109 |
| Glucose | 25.0 | 4.5 |
| Phenol red-Na | 0.043 | 0.016 |

TABLE 10-continued

DULBECCO'S MODIFIED EAGLE'S MEDIUM (DMEM) FOR THE CULTURE OF ANIMAL CELLS IN AN *IN VITRO* ENVIRONMENT

| Ingredient | mM | gm/L |
|---|---|---|
| L-Arginine | 0.39 | 0.084 |
| L-Cystine | 0.40 | 0.063 |
| L-Glutamine | 4.01 | 0.584 |
| Glycine | 0.40 | 0.030 |
| L-Histidine | 0.271 | 0.042 |
| L-Isoleucine | 0.80 | 0.105 |
| L-Leucine | 0.80 | 0.105 |
| L-Lysine | 1.01 | 0.146 |
| L-Methionine | 0.20 | 0.030 |
| L-Phenylalanine | 0.40 | 0.066 |
| L-Serine | 0.40 | 0.042 |
| L-Threonine | 0.80 | 0.095 |
| L-Tryptophan | 0.08 | 0.016 |
| L-Tyrosine | 0.60 | 0.104 |
| L-Valine | 0.80 | 0.094 |
| Choline chloride | 0.03 | 0.004 |
| Folic acid | 0.01 | 0.004 |
| myo-Inositol | 0.04 | 0.007 |
| Niacinamide | 0.04 | 0.004 |
| D-Pantothenic acid | 0.02 | 0.004 |
| Pyridoxal | 0.02 | 0.004 |
| Riboflavin | 0.001 | 0.0004 |
| Thiamine | 0.012 | 0.004 |
| Calcium chloride | 1.80 | 0.265 |
| Ferric nitrate | 0.0002 | 0.0001 |
| Magnesium sulfate | 0.83 | 0.100 |
| Potassium chloride | 5.37 | 0.400 |
| $NaCHO_3$ | 17.6 | 1.5 |
| Distilled water up to | | 1L | pH adjusted to 7.3 with 1 N HCl, filter sterilized, and stored up to 2 weeks at 4° C.
This is a general tissue culture medium for the maintenance and propagation of animal cells in an *in vitro* environment.

TABLE 11

PHOSPHATE BUFFERED SALINE (PBS) FOR CELL CULTURE MANIPULATION

| Ingredient | mM | gm/L |
|---|---|---|
| NaCL | 171.1 | 10.0 |
| KCl | 3.35 | 0.25 |
| $Na_2HPO_4$ | 6.25 | 0.75 |
| $KH_2PO_4$ | 1.84 | 0.25 |
| Distilled water up to | | 1 L |

Adjust pH to 7.3 with 1 N HCl, and filter sterilize to prevent contamination of cell cultures.
This is a general purpose saline solution used for various cell culture techniques to maintain cell integrity.

TABLE 12

ANTIBIOTIC STOCK SOLUTION FOR ADDITION TO CELL CULTURE MEDIUM TO PREVENT BACTERIAL CONTAMINATION

| Ingredient | Amount |
|---|---|
| Penicillin G-potassium salt | 500 units |
| Streptomycin sulfate | 5 mg |
| Phosphate buffered saline (PBS; Table 10) | 11 ml |

Stored at 4° C. and replaced weekly.
Penicillin and Streptomycin help prevent bacterial proliferation in cell culture *in vitro* after contamination has occurred.

TABLE 13

TRYPSIN-EDTA SOLUTION FOR DISSOCIATION OF CELLS IN TISSUE CULTURE

| Ingredient | mM | gm/L |
|---|---|---|
| Trypsin powder-porcine (1000–1500 units/mg) | — | 2.5 |
| Ethylenediaminetetraaceticacid-disodium salt (EDTA) | 1.10 | 0.4 |
| NaCl | 119.8 | 7.0 |
| $Na_2HPO_4$ | 2.50 | 0.3 |
| $KH_2PO_4$ | 1.76 | 0.24 |
| KCl | 4.96 | 0.37 |
| Glucose | 5.56 | 1.0 |
| Tris (hydroxymethyl aminomethane) | 24.80 | 3.0 |
| Phenol Red | 0.03 | 0.01 |
| Distilled water | up to | 1 L |

Filter sterilized and aliquoted into 10 ml tubes, then frozen at −20° C.
Trypsin is an enzyme protease that dissociates cell clumps into a single cell suspension for passage of cells in tissue culture. The frozen solution is thawed and warmed to 37° C. before use.

TABLE 14

FIBROBLAST CELL CULTURE MEDIUM FOR THE MAINTENANCE AND PROLIFERATION OF CELLS *IN VITRO*

| Ingredient | Volume (ml) |
|---|---|
| DMEM (Table 10) | 449.0 |
| Pen-Strep stock (Table 8) | 1.0 |
| Fetal bovine serum (FBS; heat inactivated) | 50.0 |

Filter sterilized, stored at 4° C., and used within 2 weeks. Warm to 37° C. before use with STO cells.
This medium allows the growth and maintenance of the transformed fibroblast cell line STO in tissue culture.
For STO and primary embryonic fibroblast feeder layers.

TABLE 15

MOUSE ES-cell CULTURE MEDIUM FOR THE ISOLATION AND MAINTENANCE OF MURINE ES-cells *IN VITRO*

| Ingredient | mM | gm/L | Volume (ml) |
|---|---|---|---|
| DMEM (Table 10) | — | — | 80.0 |
| Fetal bovine serum (FBS; heat inactivated) | — | — | 20.0 |
| Antibiotic stock (Table 12) | — | — | 1.0 |
| Mercaptoethanol-β stock (7 µl in 10 ml PBS) | — | — | 1.0 |
| Non-essential amino acids | | | |
| (Sigma-M 7145, St. Louis) | — | — | 1.0 |
| Containing: L-Alanine | 10.0 | 0.89 | — |
| L-Asparagine | 10.0 | 1.50 | — |
| L-Aspartic acid | 10.0 | 1.33 | — |
| L-Glutamic acid | 10.0 | 1.47 | — |
| Glycine | 10.0 | 0.75 | — |
| L-Proline | 10.0 | 1.15 | — |
| L-Serine | 10.0 | 1.05 | — |
| Nucleosides stock (Table 16) | — | — | 1.0 |

Filter sterilized, stored at 4° C., and used within 2 weeks. Warm to 37° C. before use with ES-cells.
This medium allows the isolation and proliferation of embryonal cell lines from mouse blastocysts when in co-culture with mitotically-inhibited embryonic fibroblast cells.

TABLE 16

NUCLEOSIDE STOCK SOLUTION FOR ADDITION TO TISSUE CULTURE MEDIUM

| Ingredients | mM | mg/100 ml |
|---|---|---|
| Adenosine | 3.0 | 80.0 |
| Guanosine | 3.0 | 85.0 |
| Cytidine | 3.0 | 73.0 |
| Uridine | 3.0 | 73.0 |
| Thymidine | 1.0 | 24.0 |
| Distilled water | — | 100 ml |

Filter sterilized, aliquoted, stored at 4° C., and warmed to 37° C. to re-solubilize before addition to the culture medium.
The addition of nucleosides to the culture medium of rapidly growing cell cultures aids in cell proliferation.

TABLE 17

CRYOPRESERVATION (FREEZING) MEDIUM FOR EMBRYONIC CELLS

| Ingredient | mM | Volume |
|---|---|---|
| DMEM (Table 10) | — | 60 ml |
| Dimethyl Sulfoxide (DMSO) | 0.781 | 20 ml |
| Fetal bovine serum (FBS) | — | 20 ml |

Filter sterilized, aliquoted 0.5 ml into 1.0 ml freezing vials, stored at −20° C. Thaw before addition of 0.5 ml cell suspension, cool slowly to −70° C. then freeze at −196° C.
The cryopreservation solution prevents formation of ice crystals in cells and thus allows high cell visibility.

TABLE 18

MODIFIED WHITTEN'S MEDIUM

| Ingredient | MW | gm/l | gm/100 ml | mM | mOsm |
|---|---|---|---|---|---|
| NaCl | 58.44 | 5.14 | 0.514 | 88 | 176 |
| KCl | 74.55 | 0.36 | 0.036 | 4.8 | 9.6 |
| $KH_2PO_4$ | 136.1 | 0.16 | 0.016 | 1.17 | 2.34 |
| $MgSO_4$ | 246.5 | 0.29 | 0.029 | 1.17 | 2.34 |
| $NaHCO_3$ | 84.01 | 1.9 | 0.19 | 22.6 | 45.2 |
| NaPyruvate | 110.0 | 0.035 | 0.0035 | 0.3 | 0.6 |
| CaLactate | 109.1 | 0.53 | 0.053 | 4.8 | 14.4 |
| Glucose | 180.2 | 1.0 | 0.1 | 5.5 | 5.5 |
| NaLactate | ** | 3.7 ml | 0.37 ml | 19.8 | 39.6 |
| K Pen | | 0.08 | 0.008 | — | — |
| Strep $SO_4$ | | 0.05 | 0.005 | — | — |
| Phenol Red | | 1 ml of 1% soln. | 0.1 ml of 1% soln. | | |

**MW is 112.1 anhydrous; 3.7 ml 60% syrup/l = 39.6 mOsm.
(3.7 ml/112.1 = 0.033 × .6 = 0.0198 Osm = 19.8 mOsm.)

Assays for Differentiation

11. Immunofluorescence as a Measure of Differentiation in Pluripotent Porcine Embryonic Stem Cells:

Materials
  ES-cell lines to test
  several fetal pigs
  PBS+0.1% BSA
  8 Chamber Tissue-Tek slides
  3% paraformaldehyde in 0.1 M. Sorensen's Phosphate buffer
  Primary antibodies
    Monoclonal Anti-Cytokeratin from ICN (Costa Mesa, Calif.)
    Monoclonal Anti-GFAP from ICN
    Monoclonal Anti-Neurofilament 68 from ICN
    Monoclonal Anti-Neurofilament 170 from ICN
    Monoclonal Anti-Neurofilament 200 from ICN
    Monoclonal Anti-Desmin from ICN
    Monoclonal Anti-Vimentin from ICN
  Secondary antibody
    FITC-ICN
  37° humidified incubator
  L.R. White embedding media
  Positive Control
1) Remove the brain, heart, intestine, and skeletal muscle from several fetal pigs, cut in 1 mm sections and place in glass vials.
2) Wash three times in Sorensen's buffer. Remove final buffer wash and flood vial with 3% paraformaldehyde. Fix for a minimum of 1 hour.
3) Remove fixative and wash with buffer 3 times, 5 minutes each, to remove excess fixative.
4) Dehydrate in a series of ethanol changes, 10%, 25%, 50% and three times in 70% ethanol, 10 minutes each change.
5) After the third 70% ethanol change, remove ½ of the ethanol and replace with an equal volume of L.R. White embedding media.
6) Place vial on a rotary mixer at slow speed overnight.
7) Next day, remove ½ of the White/ethanol mixture and add an equal volume of L.R. White. Let set 1 hour. Repeat 1 time.
8) Invert vial on several thicknesses of kim wipes and tap to remove all sections.
9) Put a drop of L.R. White in the tip of each BEEM capsule, and using a wooden applicator stick, pick up the sections and place in the middle of each capsule, 1 section/capsule.
10) Fill the capsules with L.R. White, taking care not to create air bubbles.
11) After all capsules are prepared, place in a 560 oven to polymerize the L.R. White. Leave in oven overnight.
12) Next day, test capsules to see if polymerization has occurred. If it has, remove block from capsule, trim and section. If it has not, leave in oven 24 hours.
13) Place sections on non-fluorescing slide, and draw circle around section using PAP pen.
14) Drop 20 μl of primary antibody solution on each section. Place in incubator for 30 minutes.
15) Remove primary antibody and wash 3 times with PBS. Check for autofluorescence.
16) Drop 20 μl of secondary antibody solution on each section. Place in incubator for 30 minutes.
17) Remove secondary antibody and wash 3 times with PBS. Allow to dry and view, then record results.
  Preparing Cells for Immunofluorescence
1) Subculture when cells are 80–90% confluent and make normal dilution of cell suspension.
2) Using a 1 ml pipet, transfer 0.3 ml cell suspension to each of the 8 chambers in the Tissue-Tek slide. Make a chamber for each of the following:
  a. each antibody
  b. blank—check for auto-fluorescence
  c. FITC only
3) After the desired number of slides are prepared, place in incubator and culture until monolayer is confluent or until desired cells are apparent. (If culture beyond 2 days, change media.)
4) When cells are ready, remove media and wash monolayer with PBS+0.1% BSA.
5) Remove final buffer wash, and flood chamber with 3% paraformaldehyde. Fix for minimum of 1 hour, but can leave on until ready to add antibody.

Primary Antibody
1) Remove fixative and wash with 0.1% BSA buffer 3 times, 10 minutes. (Leave last buffer wash on for 1 hour.)
2) Calculate volume of primary antibody needed. Each chamber will need 50l. Then prepare a 1:50 dilution using this volume. (Ex: If you need 500 μl of each Ab, then dilute 101 AB in 4901 μl 0.1% BSA buffer.)
3) Remove final buffer wash and add 50 μl of antibody to each chamber. Place in incubator for 30 minutes.
4) After incubation, flood chamber with buffer and let set 10 minutes.
5) Calculate volume of FITC needed and prepare a 1:200 dilution.
6) Remove antibody and buffer and wash 3 times in 0.1% BSA buffer.
7) Can check for auto-fluorescence at this time if you are not preparing a blank.
8) Add 50 μl FITC to each chamber and incubate for 30 minutes.
9) After incubation, flood each chamber with 0.1% BSA buffer and let set 10 minutes.
10) Remove FITC and buffer and wash 3 times with buffer. After final wash, invert slide and let dry.
11) When dry, remove chambers and gasket, then observe for fluorescence and record results.

12. Alkaline Phosphatase Staining (Talbot et al, 1993):
REAGENTS
 4% Formaldehyde in PBS
 10.8 ml of 37% formaldehyde
 89.2 ml of PBS
 Fast Red TR Salt (Sigma F-8764)
 1 mg/ml dd $H_2O$
 0.05 g in 50 ml of dd $H_2O$
 pH to 8.4 with NaOH
 Napthol AS-MX Phosphate (Light Sensitive) (Sigma N-5000)
 Stock solution: 100 mg/ml (0.1 g/1 ml dd $H_2O$) Mix 40 μl Napthol AS-MX Phosphate stock solution per ml of fast red TR salt solution needed
Controls
 POSITIVE: ES-D3 cells
 NEGATIVE: STO cells
Procedure
 1) Pour media off cells
 2) Wash once with PBS
 3) Fix with 4% formaldehyde for 15 minutes
 4) Wash with dd $H_2O$
 5) Pipet 2501 respective reagent per well and incubate for 15 minutes in a dark area
 6) Wash with $H_2O$ and store in $H_2O$ or PBS 13. Improvement in Domestic Livestock by Genetic Engineering: Genetic engineering has major advantages for improving livestock. (Ebert et al., 1991).

Mapping genes for disease resistance in animals is an expanding technology. Marker-assisted selection (MAS) and transgenic animal technology are some of the methods used in this endeavor (Lewin et al., 1991). In addition to marker assisted selection and introgression, in some cases direct selection is likely to identify and isolate single genes that can be manipulated via genetic engineering. Major genes that are isolated may be transferred into transgenic animals via ES-cells. Major genes that are isolated may be transferred into transgenic animals via ES-cells. Major genes (in addition to hormones, growth factors and their receptors) affecting quantitative traits such as growth (Schook and Clamp, 1993; Karg, 1989) and the porcine HAL gene which affects carcass growth rate, are likely candidates for suitable major genes. Lactation is a prime target for improvement by genetic alterations of hormones rather than external administration of hormones (Karg et al., 1989).

DNA technology has been shown to contribute to milk protein quality in goats. (Martin et al., 1993). These authors lament the lack of "embryo-derived stem cells from large domestic animals" (page 95) as a vehicle for gene transfer.

14. Alpha Lactalbumin (Bleck et al., 1994)

The milk protein α-lactalbumin is a component of the lactose synthase complex and is required for the synthesis of lactose in ungulates. To identify potential sequence variants within the regulatory region of this potential quantitative trait loci, the 5' flanking region of the porcine α-lactalbumin gene was sequenced for the Duroc, Yorkshire and Meishan breeds of swine. The sequenced region of the gene corresponds to 359 bp 5' of the transcription start point along with 39 bp 3' of the transcription start point. Within this sequence of the α-lactalbumin gene, two single-base pair differences were detected. One variant occurs at position −152 and the other at position −209 from the transcription start point. This region of the gene has been shown to be important in the expression and regulation of a-lactalbumin and is highly conserved among different species of mammals. Each of the variations can be detected by a restriction fragment length polymorphism within a polymerase chain reaction amplified product. The polymorphisms at the −152 and −209 positions appear to be genetically linked in the animals that have been analyzed. A number of breeds of swine were analyzed to determine whether both allelic types were present in each of the breeds. Both alleles have been shown to be present in the Duroc, Hampshire, Landrace, Meishan and Yorkshire breeds of swine. Only a single variant was observed in the Berkshire, Chester White and Pietrain breeds.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

CITED DOCUMENTS

The publications cited below are incorporated herein by reference to the extent that they supplement, explain, provide a background for, or teach methodology, techniques, and/ or compositions employed herein.

Bazer, F. W., Geisert, R. D., Zavy, M. T., 1987. Fertilization, Cleavage and Implantation. In *Reproduction in Farm Animals,* 5th edition, ed. Hafez. E.S.E., Lea & Febiger, Philadelphia, Pa.

Bearden, J. H., and J. W. Fuquay, 1980. Gestation. In, *Applied Animal Reproduction,* Reston Publishing Company, Reston, Va. pp 85–98.

Bradley, A., Evans, M., Kaufman, M. H., Robertson, E., 1984. Formation of germline chimeras from embryoderived teratorcarcinoma cell lines. *Nature* (London), 309:255–256.

Brinster et al., 1989. Targeted correction of a major histocompatibility class II Eα gene by DNA microinjected into mouse eggs. *Proc Natl Acad Sci,* 86:7087–7091.

Capecchi, Mario R., 1989. The new mouse genetics: Altering the genome by gene targeting. *Trends in genetics,* 5(3):70–76.

Clark et al., 1989. Expression of human anti-hemophilic factor IX in the milk of transgenic sheep. *Biotechnology*, Vol. 7:487–492.

Cruz, Y. P. and Pedersen, R. A., 1991. Origin of embryonic and extraembryonic cell linages in mammalian embryos. In, *Animal Application of Research in Mammalian Development*, eds. Pedersen, R. A., McLaren, A., First, N. L., Cold Spring Harbor Laboratory Press, Plainview, N.Y.

Doetschman et al., 1988. Establishment of hamster. blastocyst-derived embryonic stem (ES) cells, *Dev. Biol.*, 127: 224–227.

Ebert, K. M., et al., 1991. Changes in Domestic Livestock through Genetic Engineering, In *Current Communications* 4 Cell & *Molecular Biology, Animal Applications of Research in Mammalian Development*, ed. Pederson et al., Cold Spring Harbor Laboratory Press, 233–266.

Evans, 1990. WO90/03432.

Evans, M. J. and Kaufman, M. H. 1981. Establishment in culture of pluripotential cells from mouse embryos. *Nature*, 292:154–156.

Flake, A. W. et al., 1986. Transplantation of fetal hematopoietic stem cells in utero: the creation of hematopoietic chimeras. *Science*, vol. 233.

Frohman and Martin, 1989. Cut, paste, and save: New approaches to altering specific genes in mice. *Cell*, 56:145–147.

Gossler, A., Doetschman, T., Korn, R., Serfling, E., Kemler R. 1986. Transgenesis by means of blastocyst-derived embryonic stem cell lines. *Proc. Natl. Acad. Sci. USA*, 83:9065–9069.

Hagen, D. R., Prather, R. S., Sims, M. L., First, N. L. (1991) *J. Anim. Sci.* 69:1147–1150.

Handyside, A., Hooper, M. L., Kaufman, M. H., Wilmut, I., 1987. Towards the isolation of embryonal stem cell lines from sheep. *Roux's Arch. Dev. Biol.*, 196, 185–190.

Hasty et al., 1991. The length of homology required for gene targeting in embryonic stem cells. *Molecular and Cellular Biology*, 11(11):5586–5591.

Hooper, M. C., 1987. *Teratocarcinomas and Embryonic Stem Cells: A Practical Approach*, ed. Robertson E. J. IRL Press, Ltd., oxford, UK., 51–70.

Jasin and Berg, 1988. Homologous integration in mammalian cells without target gene selection. *Genes & Development*, 2:1353–1363.

Jeannotte et al., 1991. Low level of Hox1.3 gene expression does not preclude the use of promoterless vectors to generate a targeted gene disruption. *Molecular and Cellular Biology*, 11(11):5578–5585.

Karg, H., 1989. Manipulation of Growth, In *Biotechnology for Livestock Production*, Plenum Press, New York and London. 18:159–180.

Karg H., et al., 1989. Manipulation of Lactation, In *Biotechnology for Livestock Production*, Plenum Press, New York and London. 19:181–206.

Lewin, H. A., et al., 1991. Mapping Genes for Resistance to Infectious Diseases in Animals, In *Gene-Mapping Techniques and Applications*, Marcel Dekker, Inc., 13:283–304.

Mansour et al., 1988. Disruption of the proto-oncogene int-2 in mouse embryo-derived stem cells: A general strategy for targeting mutations to non-selectable genes. *Nature*, 336:348–352.

Martin, G., 1981, Isolation of a pluripotent cell line from early mouse embryos cultured in medium conditioned by teratocarcinoma stem cells, *PNAS* 78:7634–7638.

Martin, P., et al., 1993. Improvement of milk protein quality by gene technology, *Livestock Production Science* 35:95–115.

McLaren, A. & Bowman, P. (1969) *Nature* (London) 224, 238–240.

Mintz, B. (1965) *Science* 148, 1232–3.

Morgenstern and Land, 1990. *Nucleic Acids Res.* 18:3587–3596.

Mortensen et al., 1992. Production of homozygous mutant ES cells with a single targeting construct. *Molecular and Cellular Biology*, 12(5):2391–2395.

Notarianni et al., 1990. Maintenance and differentiation in culture of pluripotential embryonic cell lines from pig blastocysts, *J. Reprod. Fert. Suppl.*, 41, 51–56.

Papaioannou, V. E., Evans, E. P., Gardner, R. L., and Graham, C. F., 1979. Growth and differentiation of an embryonal carcinoma cell line (C145b). *J. Embroyl. exp. Morph.*, 54, 277–295.

Phillips, R. W. & Tumbleson, M. E., 1986. Models. In, *Swine in Biomedical Research*, ed. Tumbleson, M. E., Vol. 1 (Plenum Press, New York), 437–440.

Piedrahita, J. A., Anderson, G. B., BonDurrant, R. H. 1990a. Influence of feeder layer on the efficiency of isolation of porcine embryo-derived cell lines. *Therio.*, 34:865–877.

Piedrahita, J. A., Anderson, G. B., BonDurrant, R. H. 1990b. On the isolation of embryonic stem cells: Comparative behavior of murine, porcine and ovine embryos. *Therio.*, 34:879–901.

Polge, C., 1982. Embryo transplantation and preservation, In: Cole, D. J. A., Foxcroft, GTR. (eds), *Control of Pig Reproduction*, London; Butterworth Scientific; 1982:277–291.

Robertson, E. J., 1987. Embryo-derived stem cell lines, in Teratocarcinomas and Embryonic Stem Cells: a *Practical approach*, ed. Robertson, IRL Press, Ltd., Oxford, England, 71–112.

Robertson, E. J. 1987. Pluripotential stem cell lines as a route into the mouse germ line. *Trends Genet.*, 2:9–13.

Robertson, E. J. (1987) in Teratocarcinomas and Embryonic Stem Cells—a practical approach, ed. Robertson, E. J. IRL Press Ltd., Oxford, UK pgs. 71–122.

Rossant, J. and McBurney, M. W., 1982. The developmental potential of a euploid male teratocarcinoma cell line after blastocyst injection. *J. Embroyl. exp. Morph.*, 70, 99–112.

Rossant, J. and Papaioannou, V. E., 1984. The relationship between embryonic, embryonal carcinoma and embryo-derived stem cells. *Cell Differentiation*, 15, 155–161.

Rudnicki, M. A. and McBurney, M. W., 1987. Teratocarcinomas and Embryonic Stem Cells: A Practical Approach, Methods and *Induction of Differentiation in Embryonal Carcinoma Cell Lines*, ed. Robertson, IRL Press Limited, Oxford, England, 19–49.

Schook, L. B. et al., 1993. Mapping Genes for Growth and Development, In *Growth of the Pig*, ed. Hollis, CAB International, Wallingford, UK, 4:75–92.

Smith, A. G. and M. L. Hooper, 1987. Buffalo Rat Liver Cells Produce a Diffusible Activity which Inhibits the Differentiation of Murine Embryonal Carcinomas and Embryonic Stem Cells. *Dev. Biol.*, 121:9.

Stevens, L. C., 1970. The development of transplantable teratocarcinomas from intratesticular grafts of pre- and postimplantation mouse embryos. *Dev. Biol.*, 21, 364–382.

Strojek, R. M. et al., 1990. A method for cultivating morphologically undifferentiated embryonic stem cells from porcine blastocysts. *Herrogenology*, 33:901–913.

Talbot, N. C., C. E. Rexroad, Jr., V. G. Pursel, & A. M. Powell, 1993. Alkaline phosphatase staining of pig and sheep epiblast cells in culture. *Molecular Reproduction and Development*, 36:139–147.

Thomas, K. R., Capecchi, M. R., 1987. Site-directed mutagenesis by gene targeting in mouse embryo-derived stem cells. *Cell,* 51(3):503–512.

Thomas et al., 1992. High-fidelity gene targeting in embryonic stem cells by using sequence replacement vectors. *Molecular and Cellular Biology,* 12(7):2919–2923.

Wall, R. J., Pursel, V. G., Shamay, A., McKnight, R. A., Pittius, C. W. and Henninhausen, L., 1991. High-level synthesis of a heterologous milk protein in the mammary glands of transgenic swine. *Proc. Natl. Acad. Sci. USA,* 88, 1696–1700.

Ware, C. B. et al., 1988. Development of embryopnic stem cell lines from farm animals. *Biology of Reproduction,* supplement, Vol. 38.

Webel, S. K., Peters, J. B., Anderson, L. L., 1970. Synchronous and asynchronous transfer of embryos in the pig. *J. Animal Science,* 30:565–568.

Yates et al., 1985. *Nature,* 313:811–815.

What is claimed is:

1. A method for making a chimeric ungulate comprising:
    (a) introducing at least one a cultured ungulate embryonic stem cell from a cultured ungulate embryonic stem cell line, wherein said cells grow in multilayers and wherein said embryonic stem cells have a rounded shape as observed with the light microscope, a diameter of approximately 8–15 microns, and a cytoplasmic to nuclear diameter ratio of approximately 10–25; 75–90 as show in FIG. 2, wherein the ratio is approximated by the cytoplasmic diameter from the periphery of the nucleus to the end of the cell, to the diameter of the nucleus, and said cell has a first genetic complement, into a recipient embryo of the same species as the embryonic stem cell, said recipient embryo having a second genetic complement which differs from the first genetic complement, in at least one gene, to form a chimeric ungulate embryo; and
    (b) placing the chimeric ungulate embryo in an environment suitable for the completion of development to form a chimeric ungulate.

2. The method of claim 1, within the ungulate embryonic stem cell is pluripotent.

3. The method of claim 1, wherein the embryonic stem cell is introduced into the embryo at a pre-implantation stage.

4. The method of claim 3, wherein the pre-implantation stage is the blastocyst stage.

5. The method of claim 1, wherein the embryonic stem cell is derived from a first breed of ungulate and the recipient embryo is derived from a second breed of the same species as the first breed.

6. The method of claim 1, wherein the first genetic complement comprises an exogenous nucleotide sequence stably integrated into the genetic complement of the embryonic stem cell by cell line transformation.

7. The method of claim 6, wherein the first genetic complement comprises a nucleotide sequence capable of being expressed to provide human Factor IX in recoverable form from the chimeric ungulate.

8. The method of claim 6, wherein the first genetic complement comprises a nucleotide sequence encoding a protein selected from the group consisting of human blood proteins, human hormones, human growth factors, human cytokines, human enzymes human hormone receptors, human binding proteins, antigens, translation factors, transcription factors, onco-proteins, protooncoproteins, human milk proteins, and human muscle proteins.

* * * * *